(12) United States Patent
Choi et al.

(10) Patent No.: US 11,951,337 B2
(45) Date of Patent: Apr. 9, 2024

(54) MASK APPARATUS

(71) Applicant: LG Electronics Inc., Seoul (KR)

(72) Inventors: Chiyoung Choi, Seoul (KR); Taeun Heo, Seoul (KR); Hojung Kim, Seoul (KR); Wansu Youn, Seoul (KR); Sangkyun Baek, Seoul (KR); Yeongcheol Mun, Seoul (KR); Keonwang Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 569 days.

(21) Appl. No.: 17/174,766

(22) Filed: Feb. 12, 2021

(65) Prior Publication Data

US 2021/0402223 A1 Dec. 30, 2021

(30) Foreign Application Priority Data

Jun. 30, 2020 (KR) .................. 10-2020-0080437

(51) Int. Cl.
*A62B 18/08* (2006.01)
*A61B 5/08* (2006.01)
(Continued)

(52) U.S. Cl.
CPC ............ *A62B 18/08* (2013.01); *A62B 18/006* (2013.01); *A62B 7/10* (2013.01); *A62B 23/02* (2013.01)

(58) Field of Classification Search
CPC ............ A62B 7/00–14; A62B 9/00–06; A62B 18/00–025; A62B 18/08–10;
(Continued)

(56) References Cited

U.S. PATENT DOCUMENTS

| 4,546,793 A | 10/1985 | Stupecky |
| 4,646,732 A | 3/1987 | Chien |
| 5,062,421 A | 11/1991 | Burns et al. |
| 5,372,130 A | 12/1994 | Stern et al. |

(Continued)

FOREIGN PATENT DOCUMENTS

| CN | 1455270 | 11/2003 |
| CN | 103505788 | 1/2014 |

(Continued)

OTHER PUBLICATIONS

Korean Office Action in Korean Appln. No. 2020-070885882, dated Dec. 15, 2020, 19 pages (with English translation).

(Continued)

*Primary Examiner* — Michelle J Lee
(74) *Attorney, Agent, or Firm* — Fish & Richardson P.C.

(57) ABSTRACT

A mask apparatus including a mask body that defines a communication hole, a sensor mounting portion that extends from a front surface of the mask body, that surrounds the communication hole, and that defines an installation space therein, a seal coupled to a rear surface of the mask body and configured to define a breathing space between the mask body and a user, a pressure sensor accommodated in the installation space and configured to sense air pressure inside the breathing space that is in communication with the communication hole, and a film disposed in the installation space and configured to restrict permeation of moisture from the breathing space into the installation space through the communication hole.

18 Claims, 17 Drawing Sheets

(51) Int. Cl.
*A62B 18/00* (2006.01)
*A62B 18/02* (2006.01)
*A62B 5/00* (2006.01)
*A62B 7/10* (2006.01)
*A62B 23/02* (2006.01)
*C08J 5/18* (2006.01)
*C08J 9/00* (2006.01)

(58) Field of Classification Search
CPC .............. A62B 23/00–025; A62B 5/00; A41D 13/11–1192; A61M 16/06–0677; A61B 5/08; C08J 5/18; C08J 9/00
See application file for complete search history.

(56) References Cited

U.S. PATENT DOCUMENTS

| | | |
|---|---|---|
| 5,782,234 A | 7/1998 | Bates |
| 6,213,119 B1 | 4/2001 | Brydon et al. |
| 6,543,450 B1 | 4/2003 | Flynn |
| 8,667,959 B2 | 3/2014 | Tilley et al. |
| 10,226,542 B2 | 3/2019 | Messina et al. |
| 10,342,999 B2 | 7/2019 | Song et al. |
| 10,661,104 B2 | 5/2020 | Morgan et al. |
| 11,241,594 B2 | 2/2022 | Szasz et al. |
| 2003/0052279 A1 | 3/2003 | Kikuchi |
| 2003/0066257 A1 | 4/2003 | Shovlin |
| 2003/0066527 A1 | 4/2003 | Chen |
| 2005/0145249 A1 | 7/2005 | Solyntjes et al. |
| 2006/0076012 A1 | 4/2006 | Tanizawa et al. |
| 2007/0125385 A1 | 6/2007 | Ho et al. |
| 2009/0320847 A1 | 12/2009 | Bozanic et al. |
| 2010/0101575 A1 | 4/2010 | Fedorko et al. |
| 2010/0224190 A1 | 9/2010 | Tilley et al. |
| 2010/0313892 A1 | 12/2010 | Shigematsu et al. |
| 2010/0329924 A1 | 12/2010 | Harris |
| 2011/0126713 A1 | 6/2011 | Legare et al. |
| 2014/0216475 A1 | 8/2014 | Blomberg et al. |
| 2014/0360501 A1* | 12/2014 | Guiducci .......... A61M 16/0057 128/205.23 |
| 2015/0034080 A1 | 2/2015 | Furuichi et al. |
| 2015/0047642 A1 | 2/2015 | Tucker et al. |
| 2015/0136142 A1 | 5/2015 | Blomberg |
| 2015/0151143 A1 | 6/2015 | Langford |
| 2015/0202473 A1 | 7/2015 | Curran et al. |
| 2015/0217144 A1 | 8/2015 | Skov et al. |
| 2015/0217146 A1 | 8/2015 | Skov et al. |
| 2015/0250915 A1 | 9/2015 | Pugh et al. |
| 2015/0289598 A1 | 10/2015 | Hsiung |
| 2015/0306324 A1 | 10/2015 | Ayon et al. |
| 2015/0362478 A1 | 12/2015 | Phillips |
| 2016/0001111 A1 | 1/2016 | Morgan et al. |
| 2016/0022944 A1 | 1/2016 | Chodkowski et al. |
| 2016/0030778 A1 | 2/2016 | Skov et al. |
| 2016/0030779 A1 | 2/2016 | Twu et al. |
| 2016/0074604 A1 | 3/2016 | Bronner et al. |
| 2016/0236016 A1* | 8/2016 | Ono ...................... A62B 18/02 |
| 2016/0279450 A1 | 9/2016 | Goldstein et al. |
| 2017/0136271 A1 | 5/2017 | Munster |
| 2017/0157353 A1 | 6/2017 | Olsen et al. |
| 2018/0078798 A1 | 3/2018 | Fabian et al. |
| 2018/0177965 A1 | 6/2018 | Patel |
| 2018/0185677 A1 | 7/2018 | Curran et al. |
| 2018/0236275 A1 | 8/2018 | Song et al. |
| 2018/0318457 A1 | 11/2018 | Lucio |
| 2019/0009114 A1 | 1/2019 | Han |
| 2019/0113501 A1 | 4/2019 | Jameson et al. |
| 2019/0160249 A1 | 5/2019 | Rose et al. |
| 2019/0175962 A1 | 6/2019 | Su et al. |
| 2019/0275357 A1 | 9/2019 | Palmer, Jr. et al. |
| 2020/0008539 A1 | 1/2020 | Kolasa |
| 2020/0038614 A1 | 2/2020 | Duff et al. |
| 2020/0086071 A1 | 3/2020 | Lin et al. |
| 2020/0087031 A1 | 3/2020 | Yoo et al. |
| 2020/0129650 A1 | 4/2020 | Kim et al. |
| 2020/0155877 A1 | 5/2020 | Key et al. |
| 2021/0228920 A1 | 7/2021 | Arigue et al. |
| 2021/0337891 A1 | 11/2021 | Shah et al. |
| 2021/0378325 A1 | 12/2021 | Mun et al. |
| 2021/0379412 A1 | 12/2021 | Lee et al. |
| 2021/0379418 A1 | 12/2021 | Kim et al. |
| 2021/0402222 A1 | 12/2021 | Kwon et al. |
| 2022/0016449 A1 | 1/2022 | Choi et al. |

FOREIGN PATENT DOCUMENTS

| | | |
|---|---|---|
| CN | 103751919 | 4/2014 |
| CN | 104162236 | 11/2014 |
| CN | 203943119 | 11/2014 |
| CN | 104826247 | 8/2015 |
| CN | 204637356 | 9/2015 |
| CN | 105126219 | 12/2015 |
| CN | 105167366 | 12/2015 |
| CN | 105476118 | 4/2016 |
| CN | 105495776 | 4/2016 |
| CN | 105641821 | 6/2016 |
| CN | 205285072 | 6/2016 |
| CN | 106039607 | 10/2016 |
| CN | 106235464 | 12/2016 |
| CN | 106253937 | 12/2016 |
| CN | 106730464 | 5/2017 |
| CN | 106847663 | 6/2017 |
| CN | 107149182 | 9/2017 |
| CN | 206459266 | 9/2017 |
| CN | 107224687 | 10/2017 |
| CN | 206577264 | 10/2017 |
| CN | 107308564 | 11/2017 |
| CN | 107405508 | 11/2017 |
| CN | 107735148 | 2/2018 |
| CN | 206995630 | 2/2018 |
| CN | 207011751 | 2/2018 |
| CN | 207040968 | 2/2018 |
| CN | 207041756 | 2/2018 |
| CN | 207152901 | 3/2018 |
| CN | 207604526 | 7/2018 |
| CN | 207721249 | 8/2018 |
| CN | 207836817 | 9/2018 |
| CN | 108635689 | 10/2018 |
| CN | 208145256 | 11/2018 |
| CN | 109078277 | 12/2018 |
| CN | 208403333 | 1/2019 |
| CN | 208611622 | 3/2019 |
| CN | 208694061 | 4/2019 |
| CN | 109924568 | 6/2019 |
| CN | 111135492 | 5/2020 |
| CN | 111565763 | 8/2020 |
| EP | 0558147 | 9/1993 |
| EP | 0621056 | 10/1994 |
| EP | 2913083 | 9/2015 |
| EP | 3446755 | 2/2019 |
| EP | 3446756 | 2/2019 |
| GB | 1155046 | 6/1969 |
| JP | H05137808 | 6/1993 |
| JP | 3039303 | 7/1997 |
| JP | H09225012 | 9/1997 |
| JP | 10066817 | 3/1998 |
| JP | H10165527 | 6/1998 |
| JP | 3077655 | 5/2001 |
| JP | 2003322712 | 11/2003 |
| JP | 2004364177 | 12/2004 |
| JP | 3117209 U | 1/2006 |
| JP | 2007236600 | 9/2007 |
| JP | 2011078604 | 4/2011 |
| JP | 2011078678 | 4/2011 |
| JP | 2011115449 | 6/2011 |
| JP | 2012-075793 | 4/2012 |
| JP | 2013127129 | 6/2013 |
| JP | 3196218 | 2/2015 |
| JP | 2015093036 | 5/2015 |
| JP | 2015-524337 | 8/2015 |
| JP | 2015527130 | 9/2015 |
| JP | 2016087376 | 5/2016 |
| JP | 2018000982 | 1/2018 |
| JP | 2018033905 | 3/2018 |

(56) References Cited

FOREIGN PATENT DOCUMENTS

| | | |
|---|---|---|
| JP | 2018089158 | 6/2018 |
| JP | 2018-146805 | 9/2018 |
| JP | 2019501721 | 1/2019 |
| KR | 10-1989-0000137 | 3/1989 |
| KR | 10-1995-0008732 | 8/1995 |
| KR | 1020020077357 | 10/2002 |
| KR | 20050061384 | 6/2005 |
| KR | 20100081991 | 7/2010 |
| KR | 20-2010-0009804 | 10/2010 |
| KR | 1020110067854 | 6/2011 |
| KR | 20120051735 | 5/2012 |
| KR | 200461294 | 7/2012 |
| KR | 101228403 | 1/2013 |
| KR | 101536265 | 7/2015 |
| KR | 101554664 | 9/2015 |
| KR | 101619487 | 5/2016 |
| KR | 20160062808 | 6/2016 |
| KR | 20160129562 | 11/2016 |
| KR | 20160132159 | 11/2016 |
| KR | 101733470 | 4/2017 |
| KR | 20170111132 | 10/2017 |
| KR | 20170126163 | 11/2017 |
| KR | 20180009326 | 1/2018 |
| KR | 10-2018-0012496 | 2/2018 |
| KR | 101827016 | 2/2018 |
| KR | 1020180027561 | 3/2018 |
| KR | 101849610 | 4/2018 |
| KR | 20180043234 | 4/2018 |
| KR | 20180045934 | 5/2018 |
| KR | 20180064284 | 6/2018 |
| KR | 20180091698 | 8/2018 |
| KR | 20180128040 | 11/2018 |
| KR | 10-2018-0130658 | 12/2018 |
| KR | 101925388 | 12/2018 |
| KR | 1020180135840 | 12/2018 |
| KR | 10-1942785 | 1/2019 |
| KR | 20190033299 | 3/2019 |
| KR | 1020190033299 | 3/2019 |
| KR | 10-2019-0053757 | 5/2019 |
| KR | 10-2019-0022668 | 6/2019 |
| KR | 102002878 | 7/2019 |
| KR | 1020190089188 | 7/2019 |
| KR | 1020190096496 | 8/2019 |
| KR | 102023974 | 9/2019 |
| KR | 10-2019-0119804 | 10/2019 |
| KR | 101997813 | 10/2019 |
| KR | 102065360 | 2/2020 |
| KR | 1020200033495 | 3/2020 |
| KR | 102110687 | 5/2020 |
| KR | 20200048502 | 5/2020 |
| KR | 1020200048502 | 5/2020 |
| KR | 1020200049490 | 5/2020 |
| KR | 1020200079925 | 7/2020 |
| TW | 201201879 | 1/2012 |
| TW | M555232 | 2/2018 |
| TW | 201904614 | 2/2019 |
| WO | WO 1996/22124 | 7/1996 |
| WO | WO2009067583 | 5/2009 |
| WO | WO2010070495 | 6/2010 |
| WO | WO2014020469 | 2/2014 |
| WO | WO 2016/072868 | 5/2016 |
| WO | WO2016157159 | 10/2016 |
| WO | WO20170004313 | 1/2017 |
| WO | WO2017116174 | 7/2017 |
| WO | WO2018036902 | 3/2018 |
| WO | WO2018147941 | 8/2018 |
| WO | WO 2019/059699 | 3/2019 |
| WO | WO2020055106 | 3/2020 |
| WO | WO2020094850 | 5/2020 |

OTHER PUBLICATIONS

Office Action in Japanese Appln. No. 2020-204668, dated Feb. 7, 2022, 12 pages (with English translation).
Office Action in Korean Appln. No. 10-2020-0080437, dated Feb. 21, 2022, 13 pages (with English translation).
Office Action in Korean Appln. No. 10-2020-0068421, dated Jan. 23, 2022, 12 pages (with English translation).
Decision to Grant a Patent in Japanese Appln. No. 2021-043251, dated Oct. 25, 2022, 5 pages (with English translation).
Office Action in European Appln. No. 20217533.7, dated Nov. 23, 2022, 5 pages.
Office Action in European Appln. No. 21182279.6, dated Oct. 17, 2022, 2 pages.
Office Action in Taiwanese Appln. No. 110117972, dated Oct. 7, 2022, 14 pages (with English translation).
Office Action in United States U.S. Appl. No. 17/170,035, dated Sep. 29, 2022, 19 pages.
Written Decision on Registration in Korean Appln. No. 10-2020-0080437, dated Oct. 22, 2022, 11 pages (with English translation).
Extended European Search Report in European Appln. No. 21169773.5, dated Sep. 24, 2021, 4 pages.
Extended European Search Report in European Appln. No. 21169777.6, dated Sep. 24, 2021, 5 pages.
Office Action in Chinese Appln. No. 202011089763, dated Feb. 11, 2023, 18 pages (with English translation).
Office Action in Chinese Appln. No. 202011328031, dated Feb. 15, 2023, 18 pages (with English translation).
Office Action in Chinese Appln. No. 202110184702, dated Mar. 18, 2023, 23 pages (with English translation).
Office Action in Korean Appln. No. 20210129533, dated Mar. 28, 2023, 18 pages (with English translation).
Office Action in Korean Appln. No. 20220126062, dated Mar. 23, 2023, 23 pages (with English translation).
Office Action in U.S. Appl. No. 17/170,035, dated Feb. 8, 2023, 8 pages.
Extended European Search Report in European Appln. No. 21169778.4, dated Oct. 15, 2021, 5 pages.
Extended European Search Report in European Appln. No. 21169793.3, dated Oct. 15, 2021, 4 pages.
Extended European Search Report in European Appln. No. 21169796.6, dated Oct. 18, 2021, 4 pages.
Extended European Search Report in European Appln. No. 21169813.9, dated Oct. 20, 2021, 4 pages.
Extended European Search Report in European Appln. No. 21169817.0, dated Oct. 14, 2021, 4 pages.
Extended European Search Report in European Appln. No. 21170476.2, dated Oct. 13, 2021, 4 pages.
Extended European Search Report in European Appln. No. 21170861.5, dated Oct. 25, 2021, 4 pages.
Office Action in U.S. Appl. No. 17/178,103, dated Jun. 30, 2023, 30 pages.
Office Action in Chinese Appln. No. 202011403700.7, dated May 4, 2023, 18 pages (with English translation).
Office Action in Chinese Appln. No. 202110096186.5, dated Jun. 3, 2023, 16 pages (with English translation).
Office Action in U.S. Appl. No. 17/230,206, dated Jun. 22, 2023, 18 pages.
Office Action in U.S. Appl. No. 17/231,472, dated Jun. 23, 2023, 23 pages.
Extended European Search Report in European Appln. No. 20217535.2, dated Jun. 22, 2021, 4 pages.
Extended European Search Report in European Appln. No. 20217537.8, dated Jun. 22, 2021, 4 pages.
Office Action in Korean Appln. No. 10-2020-0068404, dated Jun. 30, 2021, 12 pages (with English translation).
Office Action in Korean Appln. No. 10-2020-0068611, dated Jun. 30, 2021, 12 pages (with English translation).
Office Action in Taiwanese Appln. No. 109146705, dated Jul. 7, 2021, 19 pages (with English translation).
Office Action in Taiwanese Appln. No. 110102539, dated Jul. 12, 2021, 10 pages (with English translation).
Office Action in Taiwanese Appln. No. 110102540, dated Jul. 12, 2021, 19 pages (with English translation).
Office Action in Taiwanese Appln. No. 110105039, dated Jul. 12, 2021, 15 pages (with English translation).

(56) References Cited

OTHER PUBLICATIONS

Office Action in Taiwanese Appln. No. 11120021940, dated Dec. 20, 2020, 11 pages (with English translation).
Notice of Allowance in Korean Appln. No. 10-2020-0068407, dated Nov. 29, 2021, 4 pages (with English translation).
Office Action in Korean Appln. No. 10-2020-0068400, dated Dec. 27, 2021, 13 pages (with English translation).
Office Action in Korean Appln. No. 10-2020-0068412, dated Dec. 27, 2021, 15 pages (with English translation).
Office Action in Korean Appln. No. 10-2020-0080417, dated Dec. 28, 2021, 13 pages (with English translation).
Office Action in Korean Appln. No. 10-2020-0089132, dated Dec. 28, 2021, 13 pages (with English translation).
Office Action in Korean Appln. No. 10-2020-0068413, dated Nov. 17, 2021, 13 pages (with English translation).
Office Action in Korean Appln. No. 10-2020-0080087, dated Nov. 30, 2021, 15 pages (with English translation).
Office Action in Indian Appln. No. 202114007027, dated Jan. 5, 2022, 6 pages.
Office Action in Indian Appln. No. 202114003123, dated Jan. 6, 2022, 5 pages.
Office Action in Indian Appln. No. 202114008985, dated Jan. 12, 2022, 5 pages.
Office Action in Indian Appln. No. 202114003125, dated Jan. 13, 2022, 5 pages.
Office Action in Indian Appln. No. 202114007372, dated Jan. 24, 2022, 6 pages.
Notice of Allowance in Japanese Appln. No. 2020-204668, dated Aug. 16, 2022, 5 pages (with English translation).
Office Action in Chinese Appln. No. 202110552518.6, dated Jul. 4, 2022, 18 pages (with English translation).
Notice of Allowance in Korean Appln. No. 10-2020-0068413, dated May 31, 2022, 4 pages (with English translation).
Notice of Allowance in Korean Appln. No. 10-2020-0080087, dated Jun. 30, 2022, 5 pages (with English translation).
Office Action in Chinese Appln. No. 202011328161.5, dated Apr. 2, 2022, 15 pages (with English translation).
Office Action in Chinese Appln. No. 202110046911.8, dated Apr. 15, 2022, 12 pages (with English translation).
Office Action in Chinese Appln. No. 202110382635.2, dated Apr. 20, 2022, 12 pages (with English translation).
Office Action in Chinese Appln. No. 202110383659.X, dated Apr. 18, 2022, 13 pages (with English translation).
Office Action in Chinese Appln. No. 202110404827.9, dated Apr. 19, 2022, 13 pages (with English translation).
Office Action in Indian Appln. No. 202114011936, dated May 5, 2022, 5 pages.
Office Action in Japanese Appln. No. 2021-043251, dated May 10, 2022, 6 pages (with English translation).
Office Action in Japanese Appln. No. 2021-073811, dated May 10, 2022, 6 pages (with English translation).
Office Action in Japanese Appln. No. 2021-074825, dated Apr. 19, 2022, 6 pages (with English translation).
Office Action in Japanese Appln. No. 2021-090930, dated Jun. 14, 2022, 10 pages (with English translation).
Extended European Search Report in European Appln. No. 20217533.7, dated Jun. 8, 2021, 5 pages.
Korean Office Action in Korean Appln. No. 2020-0068404, dated Apr. 5, 2021, 11 pages (with English translation).
Korean Office Action in Korean Appln. No. 2020-0068407, dated Apr. 5, 2021, 11 pages (with English translation).
Korean Office Action in Korean Appln. No. 2020-0068611, dated Apr. 5, 2021, 11 pages (with English translation).
Korean Office Action in Korean Appln. No. 2020-0109160, dated Feb. 11, 2021, 21 pages (with English translation).
Notice of Allowance in U.S. Appl. No. 17/178,103, mailed on Nov. 3, 2023, 12 pages.
Office Action in Korean Appln. No. 10-2022-0126062, mailed on Sep. 26, 2023, 8 pages (with English translation).
Office Action in U.S. Appl. No. 17/230,206, mailed on Oct. 12, 2023, 19 pages.
Office Action in U.S. Appl. No. 17/231,472, mailed on Oct. 23, 2023, 19 pages.
Office Action in U.S. Appl. No. 17/244,683, mailed on Oct. 13, 2023, 21 pages.
Office Action in U.S. Appl. No. 17/112,500, mailed on Nov. 28, 2023, 14 pages.
Notice of Allowance in U.S. Appl. No. 17/244,683, mailed on Feb. 8, 2024, 14 pages.
Office Action in Chinese Appln. No.202110096186.5, mailed on Feb. 9, 2024, 7 pages (with English translation).
Office Action in U.S. Appl. No. 17/121,056, mailed on Dec. 21, 2023, 10 pages.
Office Action in U.S. Appl. No. 17/121,115, mailed on Dec. 20, 2023, 11 pages.
Office Action in U.S. Appl. No. 17/231,462, mailed on Dec. 28, 2023, 17 pages.
Office Action in U.S. Appl. No. 17/231,472, mailed on Feb. 27, 2024, 20 pages.

* cited by examiner

MASK APPARATUS

CROSS-REFERENCE TO RELATED APPLICATIONS

The present application claims the benefits of priority to Korean Patent Application No. 10-2020-0080437, filed on Jun. 30, 2020, the disclosures of which are incorporated herein by reference in their entirety.

TECHNICAL FIELD

The present disclosure relates to a mask apparatus.

BACKGROUND

A mask is a device that can cover a user's nose and mouth to prevent or reduce inhalation of germs and dust or droplet transmitting viruses or bacteria. The mask can be in close contact with the user's face to cover the user's nose and mouth. The mask can filter germs, dust, and the like, which may contained in the air flowing, and provide filtered air to the user's mouth and nose. Air containing germs and dust may pass through a body of the mask including a filter configured to block the germs and the dust.

In some cases, a mask can be equipped with a sensor for monitoring a patient. For instance, the mask can include a safe seal that includes a soft and flexible sealant on a protrusion that is in contact with the patient's face.

In some cases, when the mask is in contact with the user's face, the sensor on the mask protrusion may not be in contact with a skin of a user. In some cases, sleeping disorders, respiratory disorders, or anesthetized patients can be monitored through the sensor.

In some cases, when the mask is used for a long time, the humidity of a breathing portion (inside of the mask) can increase due to exhalation of the wearer. When the humidity of the breathing portion increases, moisture condensed on the sensor inside the mask, which can increase risk of malfunction and failure of the sensor.

SUMMARY

The present disclosure describes a mask apparatus that can reduce or prevent accumulation of mist on the sensor due to snorting or breathing. For example, the mask apparatus can help to prevent moisture from being permeated into the sensor due to droplets when the mask is used for a long time.

The present disclosure also describes a mask apparatus including a film for blocking moisture, and the film can be stably fixed to the mask apparatus.

The present disclosure further describes a mask apparatus including a pressure sensor or a waterproof film that can be easily maintained and managed.

The present disclosure further describes a mask apparatus that can accurately sense a pressure inside the mask through a sensor provided in the mask.

According to one aspect of the subject matter described in this application, a mask apparatus including a mask body that defines a communication hole, a sensor mounting portion that extends from a front surface of the mask body, that surrounds the communication hole, and that defines an installation space therein, a seal coupled to a rear surface of the mask body and configured to define a breathing space between the mask body and a user, a pressure sensor accommodated in the installation space and configured to sense air pressure inside the breathing space that is in communication with the communication hole, and a film disposed in the installation space and configured to restrict permeation of moisture from the breathing space into the installation space through the communication hole.

Implementations according to this aspect can include one or more of the following features. For example, the film can be or include a porous film. In some examples, the film can include an edge portion disposed along an edge of the porous film. In some examples, the sensor mounting portion can include a seating surface that is disposed at an inside of the sensor mounting portion and supports the edge portion of the film.

In some implementations, the film can be disposed between the pressure sensor and the communication hole. In some implementations, the sensor mounting portion can include a first portion that extends forward from the front surface of the mask body, a pair of second portions that extend downward from ends of the first portion, and a third portion that connects lower ends of the pair of second portions to each other. In some examples, the third portion can include an inclined portion that is inclined with respect to the front surface of the mask body and that extends toward the first portion. In some examples, the communication hole can be disposed closer to the third portion than to the first portion.

In some implementations, the mask apparatus can include a sensor sealing member configured to apply pressure to the film. For example, the sensor sealing member can include a cover portion that covers an opening defined at a front surface of the sensor mounting portion, and an extension portion that extends from a rear surface of the cover portion and is configured to apply pressure to the film. In some examples, an outer surface of the extension portion is in contact with an inner surface of the sensor mounting portion.

In some implementations, the mask apparatus can include a control substrate mounted on the mask body and configured to apply pressure to the cover portion, and the pressure sensor can be mounted on a rear surface of the control substrate. In some examples, the cover portion can define a sensor opening that receives the pressure sensor.

In some implementations, the mask apparatus can include a support rib that extends from the front surface of the mask body. The support rib can include a hook disposed at an end of the support rib and configured to apply pressure to an upper end of the control substrate. In some implementations, the mask apparatus can include a mask body cover that is coupled to the front surface of the mask body and covers the pressure sensor.

In some implementations, the mask apparatus can include a pair of fan modules mounted at a left side and a right side of the front surface of the mask body, respectively, and a pair of air ducts disposed on the front surface of the mask body, where each of the pair of air ducts is disposed at an outlet side of one of the pair of fan modules. The mask body can define a plurality of air outlets in the rear surface of the mask body, where the plurality of air outlets are in communication with the outlet sides of the pair of air ducts.

In some examples, the plurality of air outlets can include a pair of air outlets that are spaced apart from each other in a horizontal direction, and the communication hole can be defined at a position in a horizontal line that passes through upper ends of the pair of air outlets. In some examples, the communication hole can be defined at a position in a vertical line that bisects the mask body into left and right sides.

In some implementations, the plurality of air outlets can include a pair of air outlets that are spaced apart from each other in a horizontal direction, and the communication hole can be defined at an intersection between the vertical line and a horizontal line that passes through upper ends of the pair of air outlets. In some implementations, the plurality of air outlets can include a pair of air outlets that are defined in the breathing space.

In some implementations, the pressure sensor can be provided in the opening passing through the mask body, and the pressure sensor can be disposed adjacent to the user's nose or mouth. Therefore, the pressure of the breathing space can be accurately measured.

In some implementations, the waterproof film can be provided between the pressure sensor and the opening to help to prevent the moisture from being permeated from the breathing space to the pressure sensor. The waterproof film can help to reduce or prevent an occurrence of the failure or malfunction of the pressure sensor due to the moisture or droplets in the air introduced into the breathing space.

In some implementations, the waterproof film can be seated inside the sensor mounting portion, and the sensor sealing member can be inserted into the sensor mounting portion to press the waterproof film. The waterproof film can be stably fixed without being separated from the mask.

In some implementations, the pressure sensor is installed on the mask body and fixed to the substrate, where the substrate can apply pressure to the sensor sealing member, and the sensor sealing member can apply additional pressure to the waterproof film to improve the sealing function of the waterproof film.

In some implementations, the waterproof film, the sensor sealing member, and the substrate can have a simple assembly structure. For instance, the waterproof film, the sensor sealing member, and the substrate can be sequentially stacked, in which the pressure sensor or the waterproof film can be easily maintained and managed.

In some implementations, the mask body defines an opening that includes a first space receiving the pressure sensor, and a second space that connects the first space to the breathing space and is defined below the first space.

In some implementations, a cross-sectional area of the passage of the second space can be defined to be less than that of the passage of the first space. The flow direction of air introduced from the breathing space to the second space can be changed in the process of moving to the first space. Therefore, the pressure sensor can avoid direct contact with air including moisture discharged from the user's mouth or nose in breathing or snorting.

DETAILED DESCRIPTION

Figure 1:
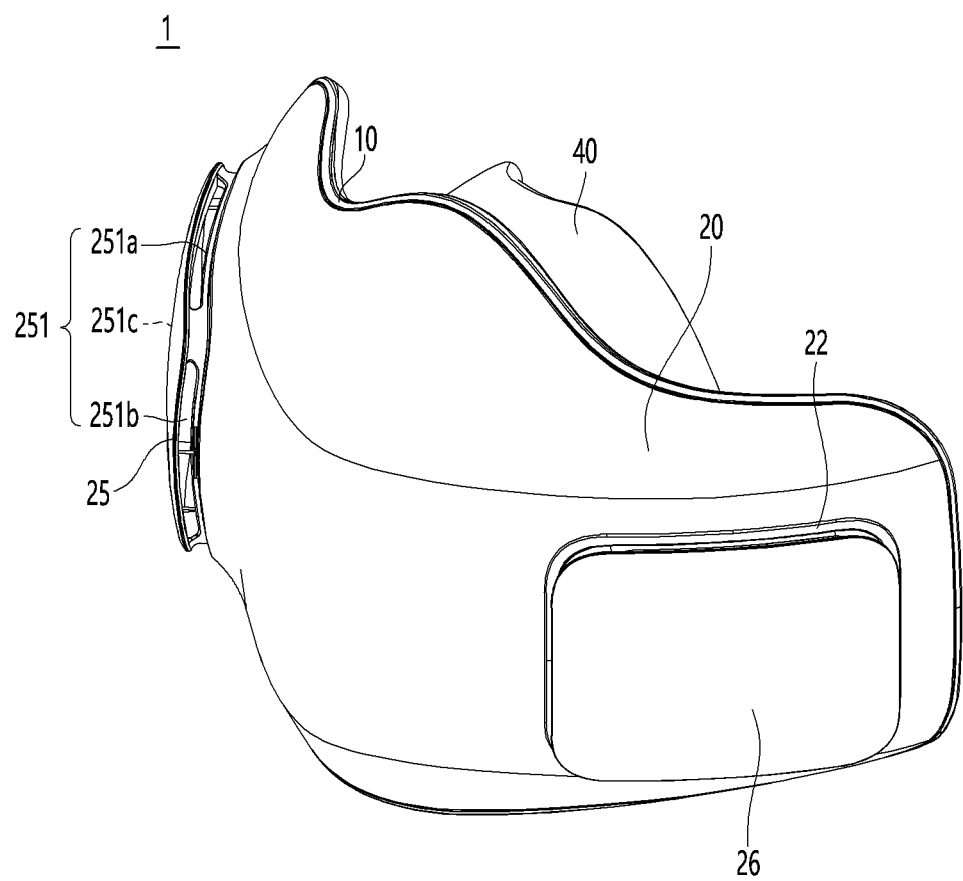
FIG. 1 is a left perspective view showing an example of a mask apparatus.
Figure 2:
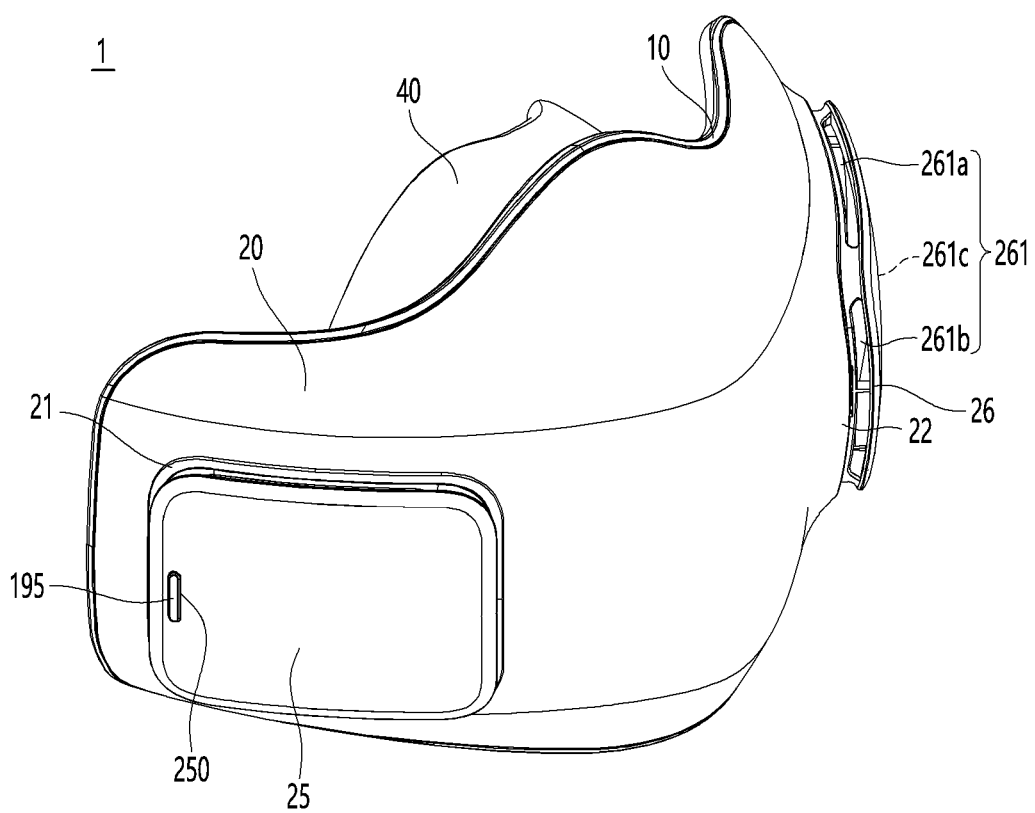
FIG. 2 is a right perspective view showing the mask apparatus.
Figure 3:
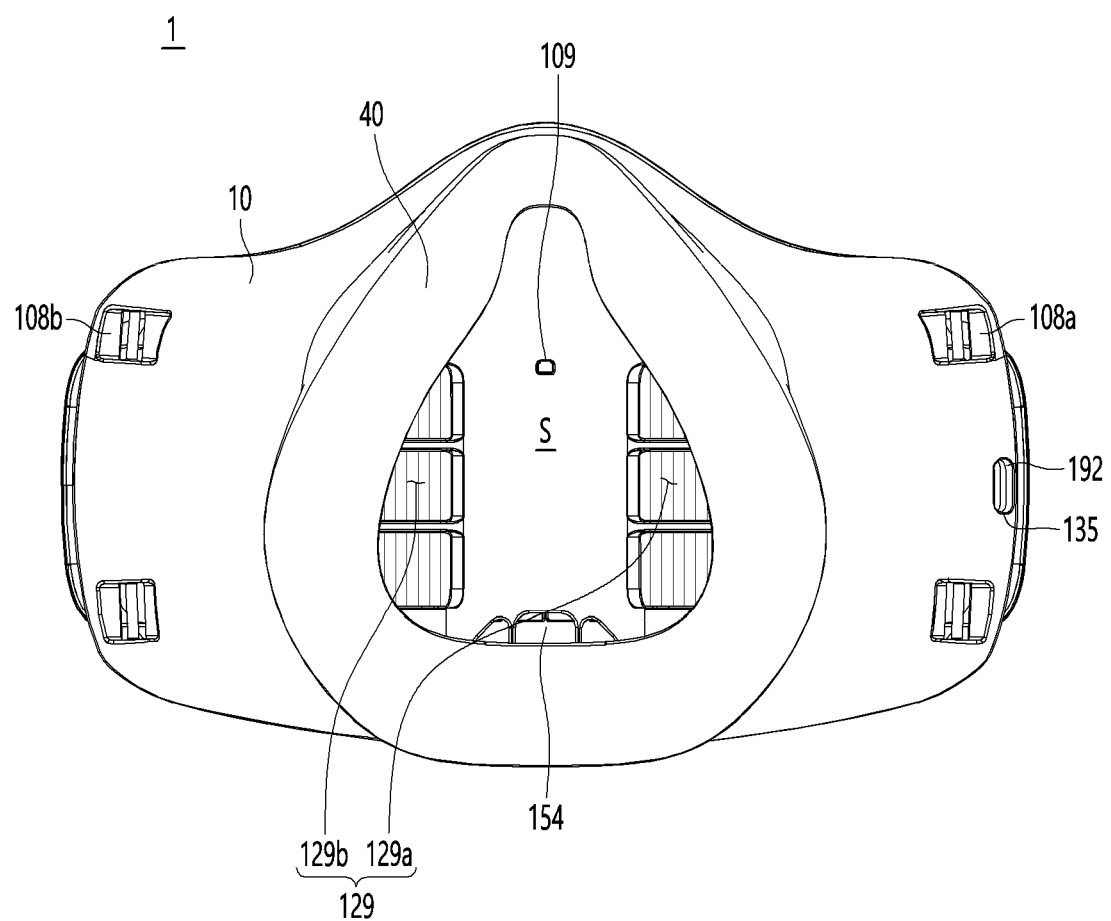
FIG. 3 is a rear view showing the mask apparatus.
Figure 4:
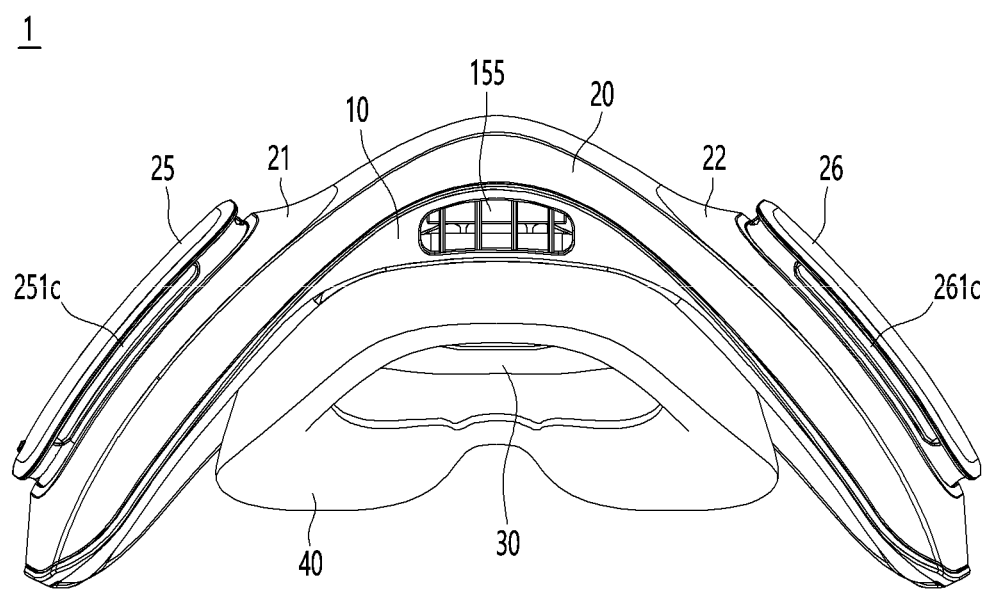
FIG. 4 is a bottom view showing the mask apparatus.

FIG. 1 is a left perspective view showing an example of a mask apparatus, FIG. 2 is a right perspective view showing the mask apparatus, FIG. 3 is a rear view showing the mask apparatus, and FIG. 4 is a bottom view showing the mask apparatus.

Referring to FIGS. 1 to 4, a mask apparatus 1 can include a mask body 10 and a mask body cover 20 coupled to the mask body 10.

The mask body 10 and the mask body cover 20 can be detachably coupled to each other. When the mask body 10 and the mask body cover 20 are coupled to each other, an inner space can be defined between the mask body 10 and the mask body cover 20. Constituents for driving the mask apparatus 1 can be disposed in the inner space. The inner space can be defined between a front surface of the mask body 10 and a rear surface of the mask body cover 20. The mask body 10 can define a rear surface of the mask apparatus 1, and the mask body cover 20 can define a front surface of the mask apparatus 1.

A rear side of the mask apparatus 1 is defined as a direction in which the rear surface of the mask apparatus 1 facing a user's face is disposed, and a front side of the mask apparatus 1 is defined as a direction which is opposite to the rear side and in which a front surface of the mask apparatus 1, which is exposed to the outside, is disposed.

The mask apparatus 1 can further include a sealing bracket 30 and a seal 40 that is detachably coupled to the sealing bracket 30.

The sealing bracket 30 can be detachably coupled to a rear surface of the mask body 10 to fix the seal 40 to the rear surface of the mask body 10. Also, when the sealing bracket 30 is separated from the rear surface of the mask body 10, the seal 40 can be separated from the mask body 10.

The seal 40 can be supported on the rear surface of the mask body 10 by the sealing bracket 30, and a breathing space S for breathing can be defined between the seal 40 and the rear surface of the mask body 10. The seal 40 can be in close contact with a user's face and can surround user's nose and mouth to restrict introduction of external air into the breathing space S.

The mask body cover 20 can include a first filter mounting portion 21 and a second filter mounting portion 22. The first filter mounting portion 21 can be disposed at a right side of the mask body cover 20, and the second filter mounting portion 22 can be disposed at a left side of the mask body cover 20.

A left direction (left side) and a right direction (right side) are defined based on the mask apparatus 1 worn on the user's face. That is, in the state in which the user wearing the mask apparatus 1, a right side of the user is defined as the right side of the mask apparatus 1, and a left side of the user is defined as the left side of the mask apparatus 1.

Also, an upward direction (upward side) and a downward direction (downward side) are defined based on the mask apparatus 1 mounted on the user's face.

A first filter cover 25 can be mounted on the first filter mounting portion 21, and a second filter cover 26 can be mounted on the second filter mounting portion 22. Filters 23 and (see FIG. 5) can be disposed inside the first filter mounting portion 21 and the second filter mounting portion 22, and the first filter cover 25 and the second filter cover 26 can cover the filter.

The first filter cover 25 and the second filter cover 26 can be detachably coupled to the first filter mounting portion 21 and the second filter mounting portion 22, respectively. For example, the first filter cover 25 and the second filter cover 26 can be coupled to be fitted into the first filter mounting portion 21 and the second filter mounting portion 22, respectively.

Each of the first filter cover 25 and the second filter cover 26 can include a front surface portion and side surface portions extending backward along an edge of the front surface portion or an edge of a rear surface.

Each of the side surface portions of the first filter cover 25 and the second filter cover 26 can have four side surfaces, and the four side surfaces can include an upper side surface, a lower side surface, a left side surface, and a right side surface.

One or a plurality of first air inlets 251 can be defined in the side surface portion of the first filter cover 25. One or a plurality of second air inlets 261 can also be defined in the side surface portion of the second filter cover 26.

In the state in which the first filter cover 25 is mounted on the first filter mounting portion 21, the first air inlet 251 can be defined to be exposed to the outside. In the state in which the second filter cover 26 is mounted on the second filter mounting portion 22, the second air inlet 261 can be defined to be exposed to the outside.

The first air inlet 251 and the second air inlet 261 can be defined in the side surfaces of the first filter cover 25 and the second filter cover 26, respectively.

In some implementations, each of the first and second air inlets 251 and 261 are respectively defined in the front surface portions of the first and second filter covers 25 and 26.

The first air inlet 251 and the second air inlet 261 can be defined at a point closer to the front surface portion from a line that bisects the side surface portion.

When a plurality of the first air inlets 251 are provided in the side surface portions of the first filter cover 25, the first air inlets 251 can include a first air suction hole 251a defined in the right side surface, a second air suction hole 251b defined in the left side surface, and a third air suction hole 251c defined in the upper side surface.

Similarly, when a plurality of the second air inlets 261 are provided in the side surface portions of the second filter cover 26, the second air inlets 261 can include a first air suction hole 261a defined in the left side surface, a second air suction hole 261b defined in the right side surface, and a third air suction hole 261c defined in the upper side surface.

An opening 250 can be defined in one of the first filter cover 25 and the second filter cover 26, and the opening 250 can be defined in an edge of one of the first filter cover 25 and the second filter cover 26. Also, a manipulation portion 195 for controlling an operation of the mask apparatus 1 can be mounted in the opening 250. In some examples, the manipulation portion 195 is mounted on the first filter cover 25 as an example.

The manipulation portion 195 can serve as a manipulation switch that turns on/off power of the mask apparatus 1. The manipulation portion 195 can be exposed to the front side of the mask apparatus 1 while being mounted in the opening 250.

The mask body 10 can include a hook mounting portion 108. The hook mounting portion 108 can be provided on the left and right sides of the mask body 10. That is, the hook mounting portion 108 can include a first hook mounting portion 108a provided at a right side of the mask body 10, and a second hook mounting portion 108b provided at a left side of the mask body 10.

Each of the first hook mounting portion 108a and the second hook mounting portion 108b can be provided in plurality to be spaced apart from each other in a vertical direction of the mask body 10. In detail, the first hook mounting portion 108a can be provided at each of the upper right and lower right sides of the mask body 10, and the second hook mounting portion 108b can be provided at each of the upper left and lower left sides of the mask body 10.

Bands for maintaining the mask apparatus 1 in close contact with the user's face can be coupled to the hook mounting portion 108.

For example, both ends of each of the bands can connect the first hook mounting portion 108a to the second hook mounting portion 108b, or two bands can respectively connect two first hook mounting portions 108a spaced apart from each other in the vertical direction to two second hook mounting portions 108b spaced apart from each other in the vertical direction to each other.

In the former case, the band can have a shape surrounding the user's occipital region, and in the latter case, the band can have a shape that is hooked on both ears of the user.

The hook mounting portion 108 can be formed by cutting a portion of the mask body 10. Thus, air can be introduced into the inner space between the mask body 10 and the mask body cover 20 through a gap defined in the hook mounting portion 108.

In detail, the external air introduced into the inner space through the hook mounting portion 108 can cool electronic components disposed in the inner space. Also, the air of which a temperature increases while cooling the electronic components can be discharged again to the outside of the mask body 10 through the hook mounting portion 108. Also, to restrict a flow of the air introduced into the inner space through the hook mounting portion 108 into the breathing space, the inside of the mask apparatus 1 can have a sealing structure.

The mask body 10 can include an air outlet 129 for supplying the filtered air to the breathing space. The user can breathe while breathing the filtered air supplied through the air outlet 129 to the breathing space.

The air outlet 129 can include a first air outlet 129a through which the filtered air introduced into the first air inlet 251 is discharged to the breathing space S and a second air outlet 129b through which the filtered air introduced into the second air inlet 261 is discharged to the breathing space S.

The first air outlet 129a can be defined at a right side with respect to a center of the mask body 10, and the second air outlet 129b can be defined at a left side with respect to the center of the mask body 10. The air introduced through the first air inlet 251 can pass through the filter 23 and then flow to the first air outlet 129a. The air introduced through the second air inlet 261 can pass through the filter 24 and then flow to the second air outlet 129b.

The mask body 10 can include air exhaust holes 154 and 155 for discharging air exhaled by the user to an external space. The air exhaust holes 154 and 155 can be defined in a lower portion the mask body 10.

The air exhaust holes 154 and 155 can include a first air exhaust hole 154 defined in a front lower end of the mask body 10 and a second air exhaust hole 155 defined in a bottom surface of the mask body 10.

In detail, a rib extending forward can be formed at the front lower end of the mask body 10, and a surface defined by the rib can be defined as the bottom surface of the mask body 10.

A flow space through the air flowing toward the second air exhaust hole 155 by passing through the first air exhaust hole 154 descends can be defined between the mask body 10 and the mask body cover 20.

A check valve can be provided in one or more of the first air exhaust hole 154 and the second air exhaust hole 155. The external air can be introduced into the breathing space, or the air discharged through the second air exhaust hole 155 can be prevented from flow backward by the check valve. The check valve can be disposed in the flow space between the first air exhaust hole 154 to the second air exhaust hole 155.

For example, the check valve having the form of a flat flap with a size and shape corresponding to the size and shape of the first air exhaust hole 154 can be provided.

In detail, an upper end of the flap can be connected to an upper edge of the first air exhaust hole 154, and when the user exhales, the flap can be bent or rotates to open the first air exhaust hole 154, and when the user inhales, the flap can be in close contact with the first air exhaust hole 154 to prevent the external air or the discharged air from being introduced again into the breathing space.

The mask body 10 can include a sensor mounting portion 109. The sensor mounting portion 109 can be equipped with a sensor for acquiring various pieces of information from the breathing space. The sensor mounting portion 109 can be disposed above the mask body 10. When the user breathes, the sensor mounting portion 109 can be disposed above the mask body 10 in consideration of a position at which a pressure change in the breathing space is constantly sensed.

The mask body 10 can include a connector hole 135.

The connector hole 135 can be an opening configured to receive a connector for supplying power to the mask apparatus 1. The connector hole 135 can be defined at either a left edge or a right edge of the mask body 10.

In some examples, since the manipulation portion 195 and the connector are connected to a power module 19 (see FIG. 5) to be described later, the connector hole 135 can be provided at one side of the left or the right side of the mask body 10, which corresponds to the position at which the power module 19 is installed.

Hereinafter, constituents of the mask apparatus 1 will be described in detail based on an exploded perspective view.

Figure 5:
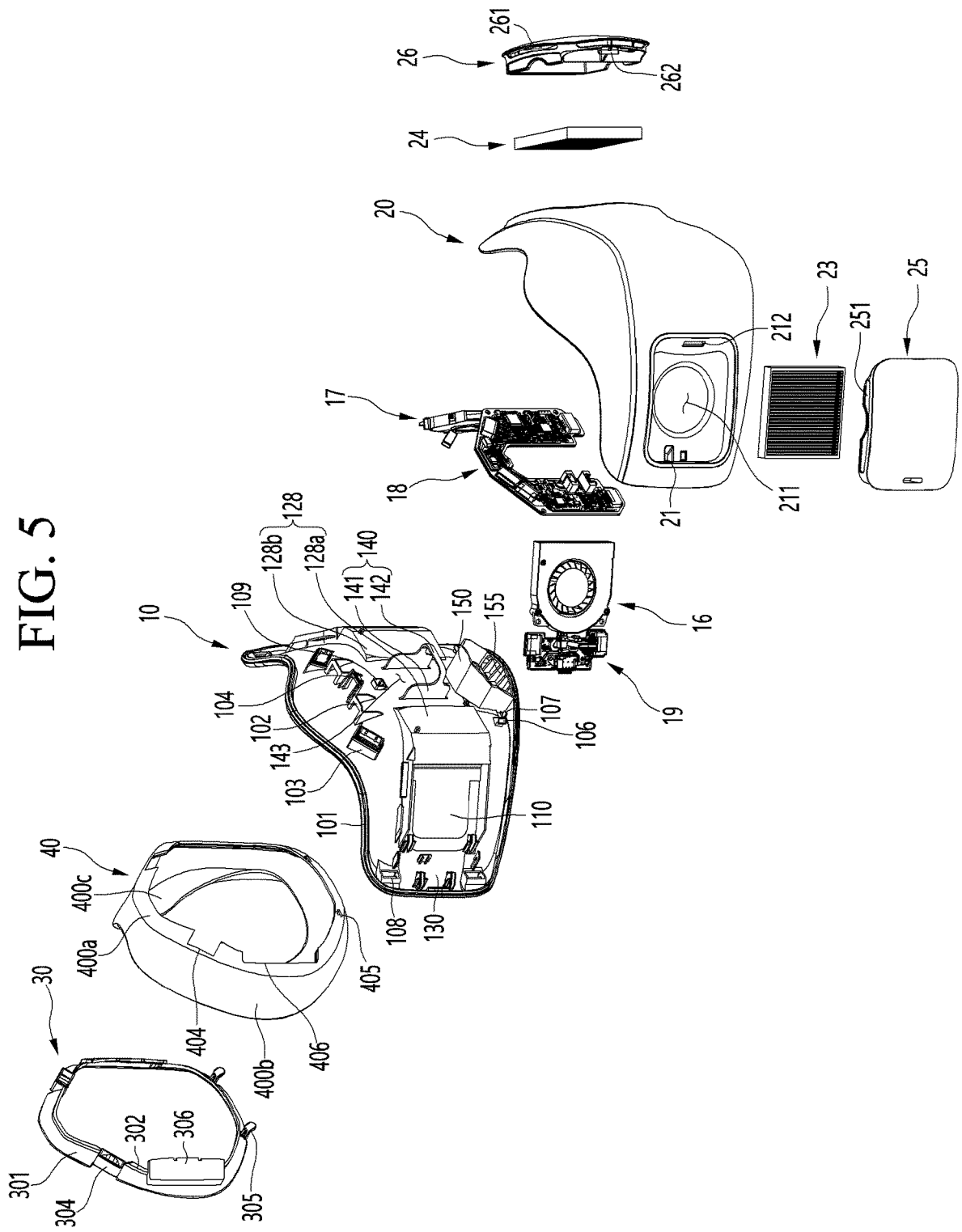
FIG. 5 is an exploded perspective view showing the mask apparatus.

FIG. 5 is an exploded perspective view showing the mask apparatus.

Referring to FIG. 5, the mask apparatus 1 can include the mask body 10, the mask body cover 20, the sealing bracket 30, and the seal 40.

In some implementations, the mask body 10 and the mask body cover 20 can be coupled to each other to form an outer appearance of the mask apparatus 1.

An inner space for accommodating components for the operation of the mask apparatus 1 can be defined between the mask body 10 and the mask body cover 20. The sealing bracket 30 and the seal 40 are coupled to the rear surface of the mask body 10 to define the breathing space between the user's face and the mask body 10 and prevent the external air from being introduced into the breathing space.

The mask body 10 can include a cover coupling groove 101. The cover coupling groove 101 can be defined along a front edge of the mask body 10. The cover coupling groove 101 can be defined by a height difference. The cover coupling groove 101 can be defined to correspond to an edge of the mask body cover 20. The cover coupling groove 101 can be defined by recessing a portion of the front surface of the mask body 10 backward. The mask body cover 20 can move toward the cover coupling groove 101 of the mask body 10 to allow the mask body cover 20 to be inserted into the cover coupling groove 101.

The mask body 10 can include a first cover coupling portion 102. An upper portion of the mask body cover 20 can be supported on the first cover coupling portion 102. The first cover coupling portion 102 can be disposed on a front upper portion of the mask body 10.

For example, the first cover coupling portion 102 can have a structure that is capable of being hook-coupled. The hook coupled to the first cover coupling portion 102 can be disposed on a rear surface of the mask body cover 20.

The first cover coupling portion 102 can be provided in plurality, and the hook can also be provided in plurality to correspond to the first cover coupling portions 102. In some examples, the first cover coupling portion 102 can be provided at the left and right sides from the center of the mask body 10, respectively. The first cover coupling portion 102 can be referred to as an upper cover coupling portion.

The mask body 10 can include a first bracket coupling portion 103. The first bracket coupling portion 103 can be disposed above the mask body 10. The first bracket coupling portion 103 can support an upper portion of the sealing bracket 30.

The first bracket coupling portion 103 can be disposed above a rear surface of the mask body 10.

For example, the first bracket coupling portion 103 can be provided by allowing a portion constituting the mask body 10 to protrude forward from the rear surface of the mask body 10. Thus, the first bracket coupling portion 103 can be understood as a recess when viewed from a rear side of the mask body 10 and a protrusion when viewed from a front side of the mask body 10.

The sealing bracket 30 can include a first body coupling portion 304 that has the same shape as the recessed shape of the first bracket coupling portion 103 and is seated on the first bracket coupling portion 103.

The first bracket coupling portion 103 can be provided at each of the left and right sides of the mask body 10. The first bracket coupling portion 103 can be defined as an upper bracket coupling portion.

The mask body 10 can include a support rib 104.

The support rib 104 can be provided to protrude forward from the front surface of the mask body 10. The support rib 104 can contact the rear surface of the mask body cover 20 when the mask body cover 20 is coupled to the mask body 10.

The mask body 10 and the mask body cover 20 can resist external forces acting in a front and rear direction by the support rib 104. The support ribs 104 can be provided in plurality on the front surface of the mask body 10.

The support rib 104 can perform a function of fixing a portion of the control module 18 mounted on the mask body 10. For this, the support rib 104 can include a hook shape.

In other words, a hook protrusion can protrude from an end of the support rib 104 to fix the end of the control module 18.

The mask body 10 can include a second cover coupling portion 106.

A lower portion of the mask body cover 20 can be supported on the second cover coupling portion 106. The second cover coupling portion 106 can protrude in a hook shape from a front lower end of the mask body 10. The first cover coupling portion 106 can be provided at each of the left and right sides from the center of the mask body 10. The second cover coupling portion 106 can be defined as a lower cover coupling portion.

A hook catching portion to which the second cover coupling portion 106 is coupled can be disposed on the mask body cover 20, and the hook catching portion can be disposed at each of left and right sides of the mask body cover 20.

The mask body 10 can include a second bracket coupling portion 107. A lower portion of the sealing bracket 30 can be supported on the second bracket coupling portion 107. The second bracket coupling portion 107 can be provided by opening the mask body 10. The second bracket coupling portion 107 can be disposed in a lower portion of the mask body 10. For example, the second bracket coupling portion 107 can be provided as a through-hole defined in the mask body 10.

A second body coupling portion 305 coupled to the second bracket coupling portion 107 can be disposed on the sealing bracket 30. The second bracket coupling portion 107 can be provided in plurality, and the second body coupling portion 305 can also be provided in plurality to correspond to the second bracket coupling portions 107. In some examples, the second bracket coupling portion 107 can be provided at each of the left and right sides with respect to the center of the mask body 10. The second bracket coupling portion 107 can be defined as a lower bracket coupling portion.

The mask body 10 can include the above-described sensor mounting portion 109.

The sensor mounting portion 109 can have a rib shape in which a portion of the front surface of the mask body 10 protrudes forward. In detail, the sensor mounting portion 109 has a rib shape that is surrounded along an edge of the sensor, and an installation space in which the sensor is installed is defined in the sensor mounting portion 109.

A hole through which the installation space and the breathing space communicate with each other is defined in the mask body 10 corresponding to the inside of the sensor mounting portion 109. The sensor disposed in the installation space can include a pressure sensor, and the pressure sensor can sense pressure information of the breathing space through the hole.

The mask body 10 can include a fan module mounting portion 110.

The fan module mounting portion 110 can include a first fan module mounting portion on which a first fan module 16 is mounted and a second fan module mounting portion on which a second fan module 17 is mounted.

The first fan module mounting portion and the second fan module mounting portion can be disposed on the front surface of the mask body 10. In detail, the first fan module mounting portion can be disposed at the right side of the mask body 10, and the second fan module mounting portion can be disposed at the left side of the mask body 10.

The first fan module 16 and the second fan module 17 can be detachably coupled to the first fan module mounting portion and the second fan module mounting portion, respectively.

The mask body 10 can include an air duct 120.

The air duct 120 can be disposed on the front surface of the mask body 10. A passage through which air passes can be provided in the air duct 120.

The air duct 120 can include a first air duct 120a (see FIG. 10) connected to the first fan module mounting portion and a second air duct 120b (see FIG. 10) connected to the second fan module mounting portion.

The first air duct and the second air duct can be disposed on an edge of the first fan module mounting portion and an edge of the second fan module mounting portion, which are adjacent to the center of the front surface of the mask body 10 so as to be disposed between the first fan module mounting portion and the second fan module mounting portion.

Also, the first fan module mounting portion and the second fan module mounting portion can have a shape symmetrical with respect to a vertical plane (or a vertical line) passing through the center of the front surface of the mask body 10. Similarly, the first air duct and the second air duct can also have a shape symmetrical with respect to the vertical plane or the vertical line passing through the center of the front surface of the mask body 10.

One end of the air duct 120 communicates with the outlet of the fan module 16 and 17 to allow the external air to be introduced into the air duct 120. In addition, the other end of the air duct 120 communicates with the air outlet 129 so that the air introduced into the air duct 120 is discharged into the breathing space S.

A control module 18 can be mounted on the front surface of the air duct 120.

A control module mounting portion 128 for mounting the control module 18 can be disposed on the front surface of the air duct 120. A portion of the front surface of the air duct 120 can be provided as a flat portion on which the control module 18 is capable of being seated, and the flat portion can be defined as the control module mounting portion 128.

The control module mounting portion 128 can include a first control module mounting portion 128a provided in the first air duct and a second control module mounting portion 128b provided in the second air duct. One control module 18 can be fixed to the first control module mounting portion 128a and the second control module mounting portion 128b, or a plurality of control modules can be respectively fixed to the first and second control module mounting portions 128a and 128b.

The mask body 10 can include a power module mounting portion 130 for mounting the power module 19.

The power module mounting portion 130 can be disposed on the front surface of the mask body 10. The power module mounting portion 130 can be provided at one of the left and the right side of the mask body 10.

The power module mounting portion 130 can be disposed at the side of the fan module mounting portion 110. Specifically, the power module mounting portion 130 can be provided between the fan module mounting portion 110 and a side end of the mask body 10. The side end of the mask body 10 can be defined as an end adjacent to the user's ear when worn. Also, the connector hole 135 can be formed in the side end of the mask body 10, which is provided with the power module mounting portion 130.

The mask body 10 can include a battery mounting portion 140 for mounting a battery.

The battery mounting portion 140 can be disposed on the front surface of the mask body 10. The battery mounting portion 140 can be provided to protrude forward from the front surface of the mask body 10 so as to surround the battery.

For example, the battery mounting portion 140 can include a pair of guide ribs protruding forward from the front surface of the mask body 10 and a connection rib connecting front ends of the pair of guide ribs to each other. Also, the battery can be mounted in a battery accommodation space defined by the pair of guide ribs and the connection rib.

The battery can move downward from an upper side of the battery accommodating space and be inserted into the battery accommodating space and then can move in a reverse direction to be separated. A lower portion of the battery inserted into the battery mounting portion 140 can be supported by an air discharge portion 150 to be described later.

The mask body 10 can include the air discharge portion 150.

The air discharge portion 150 can be disposed in a lower portion of the mask body 10. The air discharge portion 150 can define a flow space through which the air flowing from the first air exhaust hole 154 toward the second air exhaust hole 155 passes.

The air discharge portion 150 can protrude forward from the front surface of the mask body 10. Also, the air discharge portion 150 can extend to be rounded in an arch shape or can extend to be bent several times.

When the mask body cover 20 is coupled to the mask body 10, a front end of the air discharge portion 150 can be in contact with the rear surface of the mask body cover 20, and the inner space of the mask body 10 and the flow space can be partitioned from each other.

The air discharge portion 150 can define a top surface and both side surfaces of the flow space, and a rear surface of the mask body cover 20 can define a front surface of the flow space. Also, the front surface of the mask body 10 can define a rear surface of the flow space, and the bottom surface of the mask body 10 on which the second air exhaust hole 155 is defined can define a bottom surface of the flow space.

The top surface of the air discharge portion 150 can support a lower end of the battery. Both lower ends of the air discharge portion 150 having the arch shape or tunnel shape can be connected to the bottom surface of the mask body 10, and the bottom surface of the mask body 10 can be defined by the rib extending forward from the lower end of the front surface of the mask body 10. The cover coupling groove 101 is recessed along the front end of the rib defining the bottom surface of the mask body 10, and the lower end of the rear surface of the mask body cover 20 is coupled to the cover coupling groove 101.

The first air exhaust hole 154 can be defined in the front surface of the mask body 10 defining the rear surface of the flow space.

The mask body cover 20 can include a pair of filter mounting portions 21 and 22, as described above.

The filter mounting portions 21 and 22 can be provided by recessing the front surface of the mask body cover 20 by a predetermined depth toward the rear surface of the mask body cover 20. Filters 23 and 24 are accommodated inside the filter mounting portions 21 and 22, and filter covers 25 and 26 can be mounted on edges of the filter mounting portions 21 and 22 in the state in which the filters 23 and 24 are accommodated.

Air suction holes 211 and 221 can be defined in the filter mounting portions 21 and 22. The air suction holes 211 and 221 can communicate with suction holes defined in the front surfaces of the fan modules 16 and 17, respectively. Each of edges of the air suction holes 211 and 221 can have an inclined surface that inclined in a direction in which a diameter gradually decreases from the front surface to the rear surface.

A filter cover mounting groove 212 for fixing each of the filter covers 25 and 26 can be defined in a side surface of each of the filter mounting portions 21 and 22. A coupling protrusion inserted into the filter cover mounting groove 212 and 222 can be disposed on each of the filter covers 25 and 26. In FIG. 5, only the coupling protrusion 262 disposed on the left filter cover 26 is illustrated, but it is noted that the same coupling protrusion is disposed on the right filter cover 25 as well. A sealing material for sealing can be provided between the edges of the rear surfaces of the air suction holes 211 and 221 of the filter mounting portions 21 and 22 and the fan inlets of the fan modules 16 and 17. The sealing material can surround the air suction holes 211 and 221 and edges of the fan inlets of the fan modules 16 and 17 to prevent the external air from being introduced.

The filter mounting portions 21 and 22 include a first filter mounting portion 21 provided at the right side of the mask body cover 20 and a second filter mounting portion 22 provided at the left side of the mask body cover 20.

The air suction hole defined in the first filter mounting portion 21 can be defined as a first air suction hole 211, and the air suction hole defined in the second filter mounting portion 22 can be defined as a second air suction hole 221.

The filters 23 and 24 can include a first filter 23 accommodated inside the first filter mounting portion 21 and a second filter 24 accommodated inside the second filter mounting portion 22.

The filter covers 25 and 26 can include a first filter cover 25 mounted on the first filter mounting portion 21 and a second filter cover 26 mounted on the second filter mounting portion 22. A plurality of first air inlets 251 can be defined in the first filter cover 25 to allow the external air to be introduced, and a plurality of second air inlets 261 can be defined in the second filter cover 26 to allow the external air to be introduced.

The control module 18 can be referred to as a first electronic circuit component, and the power module 19 can be referred to as a second electronic circuit component.

The fan modules 16 and 17 can include a fan, a fan motor, and a fan housing accommodating the fan and the fan motor. The fan housing can include a suction hole through which the external air is introduced into the fan, and a discharge hole through which the air forcedly flowing by the fan is discharged.

The fan can include various types of fans. For example, the fan can include a centrifugal fan that suctions air from the front side of the mask body cover 20 and discharges the air to the side of the mask body 10. In some examples, the fan can include an axial fan or a cross-flow fan.

The air introduced through the first air inlet 251 to pass through the first filter 23 is suctioned through the first air suction hole 211. Also, the air introduced through the second air inlet 261 to pass through the second filter 24 is suctioned through the second air suction hole 221.

The fan outlet of the first fan module 16 can communicate with the first air duct to discharge the air to the breathing space, and the fan outlet of the second fan module 17 can communicate with the second air duct to discharge the air to the breathing space.

The control module 18 can control an operation of the mask apparatus 1. The control module 18 can be fixed to the control module mounting portion 128.

The control module 18 can include a communication module to transmit and receive various types of information. The control module 18 can include a data storage module to store various types of information.

The control module 18 can control an operation of each of the fan modules 16 and 17. In detail, the control module 18 can control the operation of each of the fan modules 16 and 17 based on information sensed from the sensor.

The control module 18 can be electrically connected to the power module 19, the fan modules 16 and 17, and the battery so as to be interlocked with each other.

The power module 19 can receive power from the outside. The power module 19 can include a charging circuit for charging the battery. The power module 19 can include the connector 192 and the manipulation portion 195. Thus, the control module 18 can be operated by receiving battery power or external power through the connector 192.

The power module 19 can control supply of power to the mask apparatus 1 by the manipulation portion 195. In detail, the power module 19 can control supply of power from the battery to the control module 18 and the fan modules 16 and 17.

The seal 40 can be coupled to the rear surface of the mask body 10 by the sealing bracket 30 to be in close contact with the user's face.

The rear surface of the mask body 10 can be to be spaced apart from the user's face by the seal 40.

The sealing bracket 30 can be provided in a ring shape forming a closed loop. The seal 40 can be detachably coupled to the sealing bracket 30.

Also, the sealing bracket 30 is coupled to be detachable from the mask body 10 to separate the sealing bracket 30 from the mask body 10. With this structure, only the sealing bracket 30 can be separated, or an assembly of the seal 40 and the sealing bracket 30 can be separated from the mask body 10 to clean only sealing bracket 30 or clean both the sealing bracket 30 and the seal 40.

After the seal 40 is coupled to the sealing bracket 30, the sealing bracket 30 is coupled to the mask body 10, then the seal 40 is stably fixed to the mask body 10.

The sealing bracket 30 can include a sealing insertion portion 301 inserted into an inner edge of the seal 40.

Figure 13:
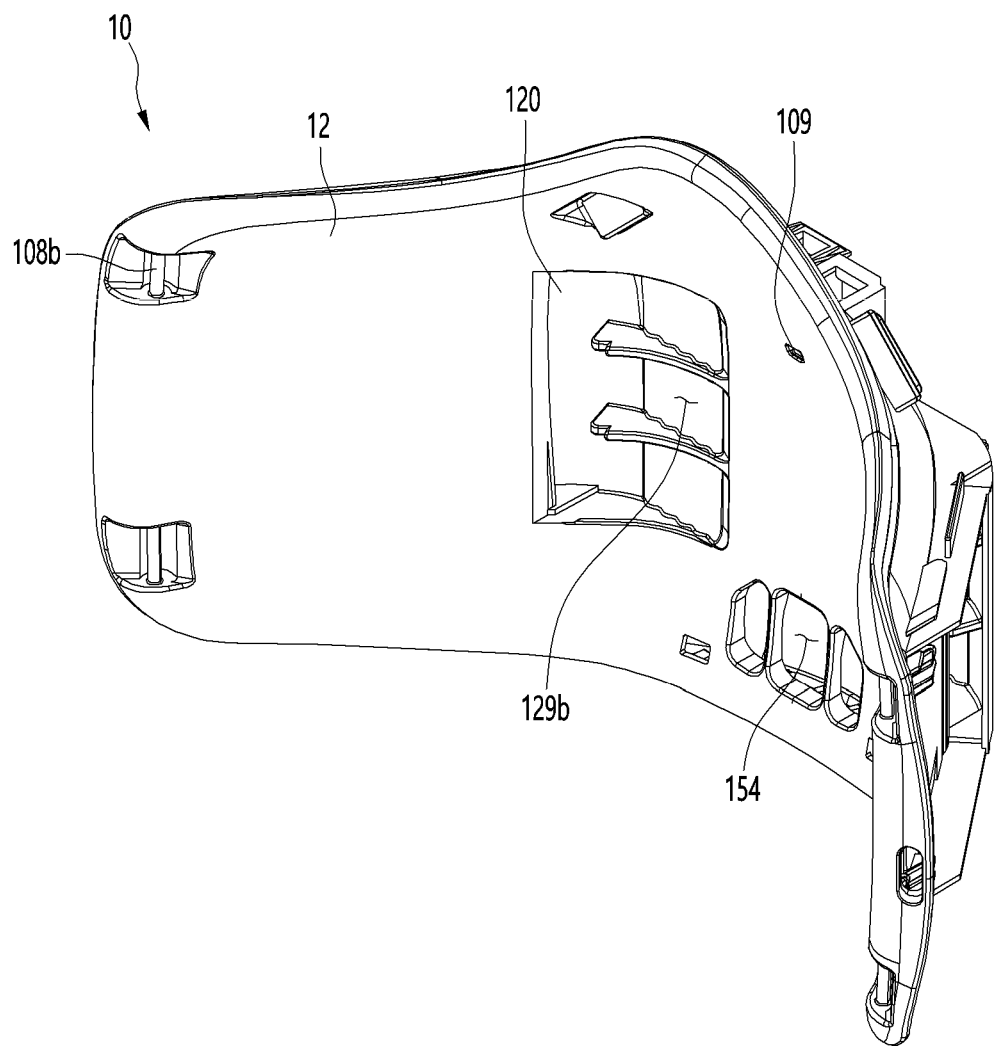
FIG. 13 is a rear perspective view showing the mask body.

The inner edge of the seal 40 can be provided in a shape of seal lips that is branched into two portions, and the sealing insertion portion 301 can be inserted into the seal lips (see FIG. 13).

The sealing insertion portion 301 can have a cross-sectional shape having a constant thickness or a cross-sectional shape of which a thickness decreases from an inner edge toward an outer edge. A body of the sealing bracket 30 can be provided by the sealing insertion portion 301 and a fixing guide 302 to be described later.

The sealing bracket 30 can include the fixing guide 302.

The fixing guide 302 can be bent at an inner end of the sealing insertion portion 301. When the sealing insertion portion 301 is completely inserted into the seal lips of the seal 40, one of the two seal lips is in contact with the fixing guide 302. That is, when the inner edge of the seal 40 is in contact with the fixing guide 302, it can be understood that the seal 40 is completely coupled to the sealing bracket 30.

The sealing bracket 30 can include a bracket insertion portion 306 coupled to the mask body 10. The bracket insertion portion 306 is inserted into a cutoff portion defined in the rear surface of the mask body 10 to cover a portion of an edge of the cutoff portion. The cutoff portion can be understood as an opening communicating with the air duct 120 so that the air passes therethrough. The bracket insertion portion 306 can be disposed on one edge of the cutoff portion, specifically, an outer edge.

The air outlet 129 already described can be understood as the remaining portion of the cutoff portion that is not covered by the bracket insertion portion 306 in a state in which the bracket insertion portion 306 is inserted into one side of the cutoff portion.

When the bracket insertion portion 306 is inserted into or coupled to the one side of the cutoff portion to shield the one side of the cutoff portion, the air discharged from the fan modules 16 and 17 can pass between the air duct 120 and the bracket insertion portion 306 to flow to the air outlet 129.

The bracket insertion portion 306 can perform a function of fixing the sealing bracket 30 to the mask body 10 while defining one surface of the air duct 120.

In detail, an upper portion of the sealing bracket 30 can be fixed to the upper portion of the mask body 10 by the first body coupling portion 304, a lower portion of the sealing bracket 30 can be fixed to the lower portion of the mask body 10 by the second body coupling portion 305, and an intermediate portion of the sealing bracket 30 can be fixed to an intermediate portion of the mask body 10 by the bracket insertion portion 306.

The seal 40 can be made of a material having elasticity. The seal 40 can be in close contact with the user's face and deformed to correspond to a facial contour of the user. The seal 40 can be provided in a ring shape forming a closed loop. The seal 40 can be provided to cover the user's nose and mouth.

The seal 40 includes a coupling portion 400*a* coupled to the mask body 10, a side surface portion 400*c* extending from the coupling portion 400*a* toward the user's face, and a contact portion 400*b* that is bent from an end of the side surface portion 400*c* to extend toward the coupling portion 400*a*.

The contact portion 400*b* can be a portion that is in close contact with the user's face, and the side surface portion 400*c* and the contact portion 400*b* can be angled at an angle of about 90 degrees or less to define a space between the side surface portion 400*c* and the contact portion 400*b*.

A first opening can be defined inside the coupling portion 400*a* of the seal 40, and a second opening can be defined inside the contact portion 400*b*. As illustrated in FIG. 3, the second opening can include a main opening in which the front of the user's nose and mouth are disposed and a sub opening extending from an upper end of the main opening and disposed on the user's nose.

Also, a lower portion of the main opening, that is, a portion that is in close contact with the front of the user's jaw can be designed closer to the mask body 10 than a portion that is in close contact with the front of the user's cheek.

In some examples, a plurality of ventilation holes can be defined in the contact portion 400*b* to minimize a phenomenon in which moisture is generated on the user's cheek. The plurality of ventilation holes can have different sizes, and as an example, a diameter of the ventilation hole can gradually increase from an inner edge to an outer edge of the contact portion 400*b*.

The air outlet 129 and the air exhaust holes 154 and 155 can be provided inside the first opening, and the user's nose and mouth can be disposed inside the second opening.

The seal 40 is disposed between the user's face and the mask body 10, and the breathing space S is defined by the coupling portion 400a, the contact portion 400b, and the inner side of the side surface portion 400c of the seal 40.

A bracket insertion groove 401 can be defined in an end of the coupling portion 400a of the seal 40.

The bracket insertion groove 401 can be understood as a groove or a space defined between the two seal lips when the coupling portion 400a has the shape that is branched into the two seal lips as described above, and the bracket insertion portion 301 of the sealing bracket 30 is inserted into the bracket insertion groove 401.

The seal 40 includes a first seating portion 404 on which the first body coupling portion 304 is seated, a second seating portion 405 on which the second body coupling portion 305 is seated, and a third seating portion 406 on which the bracket insertion portion 306 is seated.

The first and third seating portions 404 and 406 can be understood as grooves in which a portion of the seal 40 is cut to form an accommodation space in which the first body coupling portion 304 and the bracket insertion portion 306 are accommodated. Also, the second seating portion 405 can be understood as a hole in which a portion of the seal 40 is cut to pass through the second body coupling portion 305.

In another aspect, the first seating portion 404 can be defined as a first opening, the second seating portion 405 can be defined as a second opening, and the third seating portion 406 can be defined as a third opening.

Figure 6:
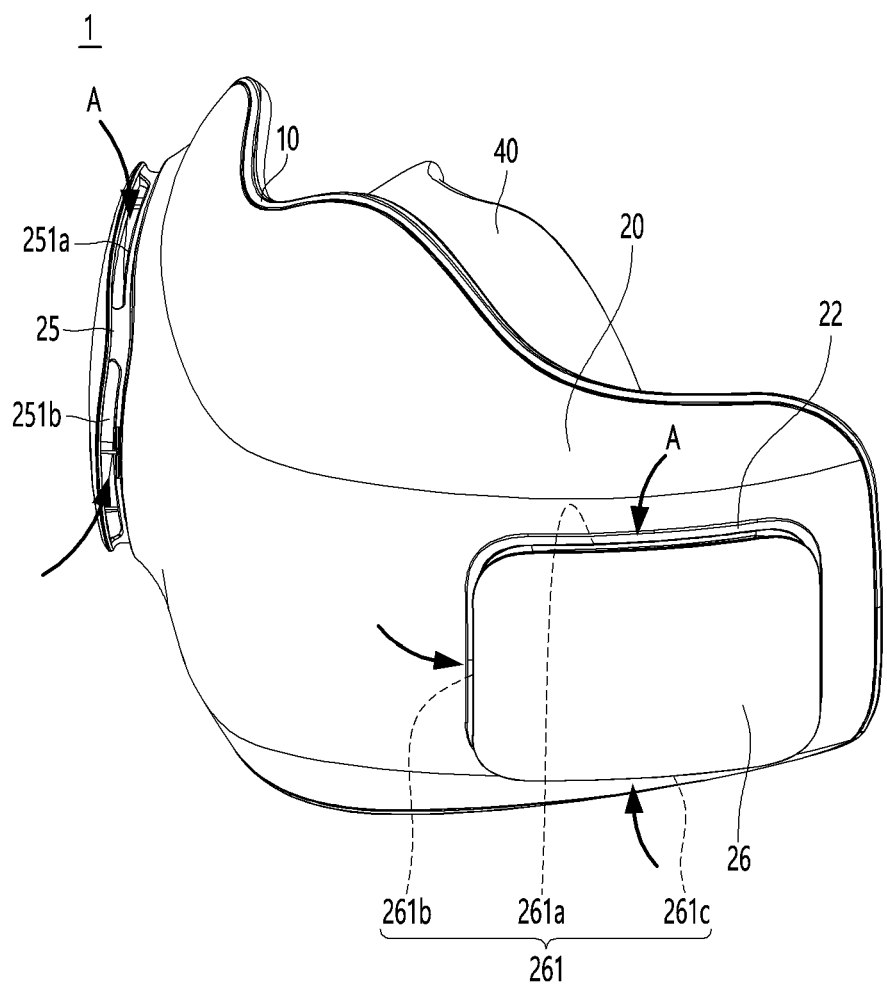
FIGS. 6 and 7 are views illustrating examples of a flow of air when the mask apparatus is operated.
Figure 7:
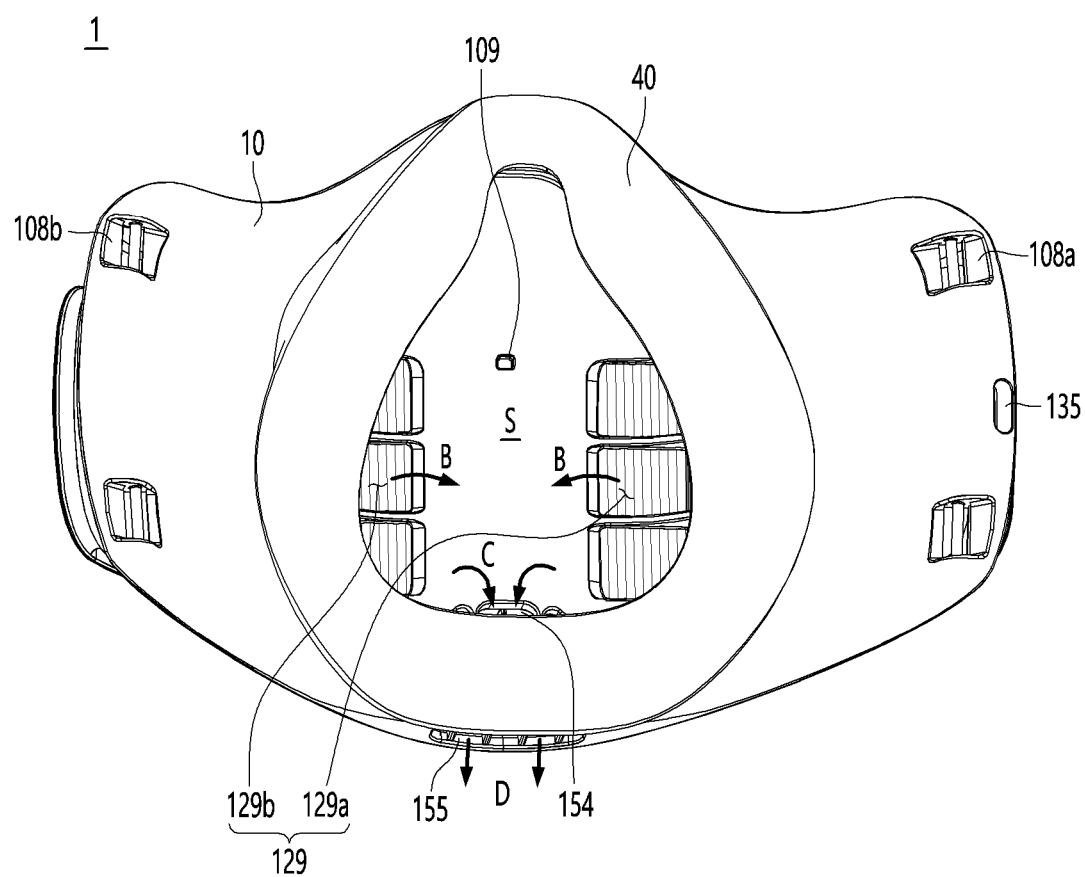

FIGS. 6 and 7 are views illustrating examples of a flow of air when the mask apparatus is operated.

Referring to FIGS. 6 and 7, the mask apparatus 1 can suction the external air through the air inlets 251 and 261 provided in the filter covers 25 and 26. The flow direction of the external air suctioned into the mask apparatus 1 is indicated by an arrow "A" Since the air inlets 251 and 261 are provided in plurality to suction the air in various directions, an inflow rate of the external air increases.

For example, the air inlets 251 and 261 can include air inlets 251a and 261a configured to suction air flowing at upper sides of the filter covers 25 and 26, air inlets 251b and 261b configured to suction air flowing at a front side of the filter covers 25 and 26, and air inlets 251c and 261c configured to suction air flowing at a lower side of the filter covers 25 and 26. The side air inlets 251b and 261b can be provided at one or both sides of the left and right sides of the filter covers 25 and 26.

Since the filter covers 25 and 26 in which the air inlets 251 and 261 are provided are respectively disposed at left and right sides of the front surface of the mask apparatus 1, the external air can be smoothly suctioned from the left and right sides of the front surface of the mask apparatus 1.

The external air introduced through the air inlets 251 and 261 can be filtered by passing through the filters 23 and 24 disposed inside the filter mounting portions 21 and 22. The filters 23 and 24 can be replaced when the filter covers 25 and 26 are separated from the mask apparatus 1.

The air passing through the filters 23 and 24 can be introduced into the suction holes of the fan modules 16 and 17 through the air suction holes 211 and 221. Since the filter mounting portions 21 and 22 in which the air suction holes 211 and 221 are defined and the fan modules 16 and 17 are assembled in the state of being in close contact with each other, the air passing through the filter can be prevented from leaking, or the external air can be prevented from being introduced between the filter mounting portions 21 and 22 and the fan modules 16 and 17.

The air discharged through the fan outlets of the fan modules 16 and 17 can pass through the air duct 120 to flow into the breathing space S through the air outlet 129. A flow direction of the air introduced into the breathing space S through the air outlet 129 is indicated by an arrow "B."

The breathing space S can be defined by the mask body 10 and the seal 40. When the mask body 10 is put on the user's face, the seal 40 can be in close contact with the mask body 10 and the user's face to form an independent breathing space that is separated from the external space.

The air that the user exhales after suctioning the filtered air supplied through the air outlet 129 can be exhausted to the external space through the air exhaust holes 154 and 155.

As described above, the air exhaust holes 154 and 155 include a first air exhaust hole 154 communicating with the breathing space and a second air exhaust hole 155 communicating with the external space, and the first air exhaust hole 154 and the second air exhaust hole 155 can communicate with each other by the flow space defined by the air discharge portion 150. The air exhaled by the user can be guided into the flow space through the first air exhaust hole 154. A flow direction of the air flowing into the flow space through the first air exhaust hole 154 is indicated by an arrow "C."

The air guided into the flow space through the first air exhaust hole 154 can be discharged to the external space through the second air exhaust hole 155. A flow direction of the air flowing to the external space through the second air exhaust hole 155 is indicated by an arrow "D."

Figure 8:
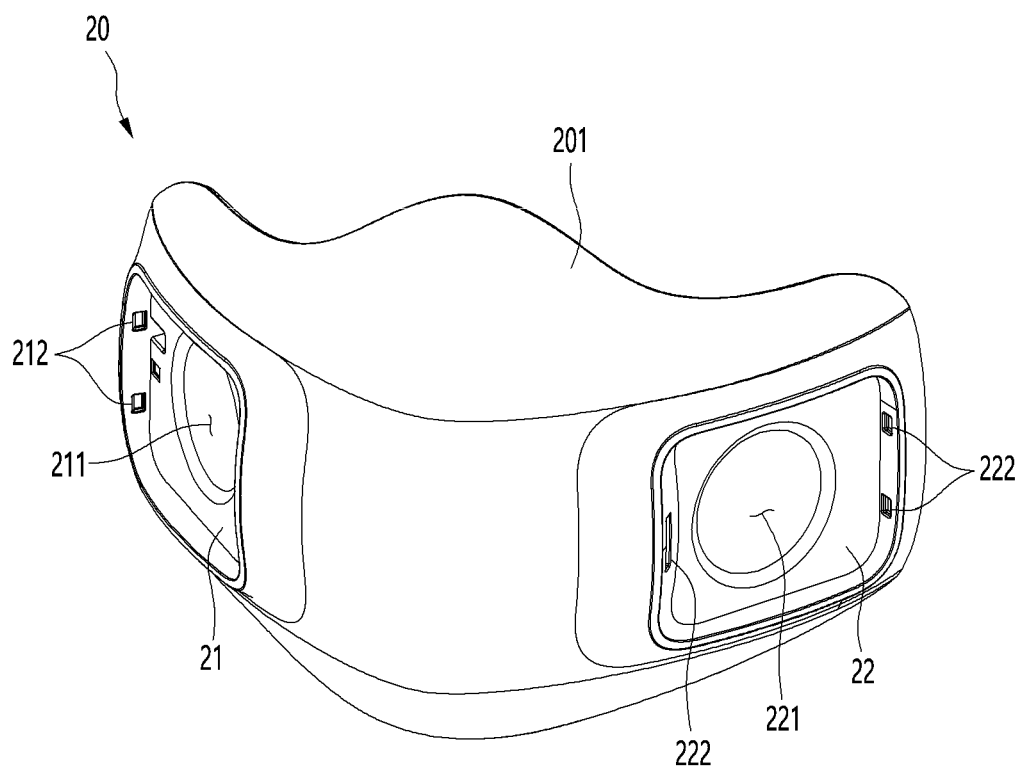
FIG. 8 is a front perspective view showing an example of a mask body cover.
Figure 9:
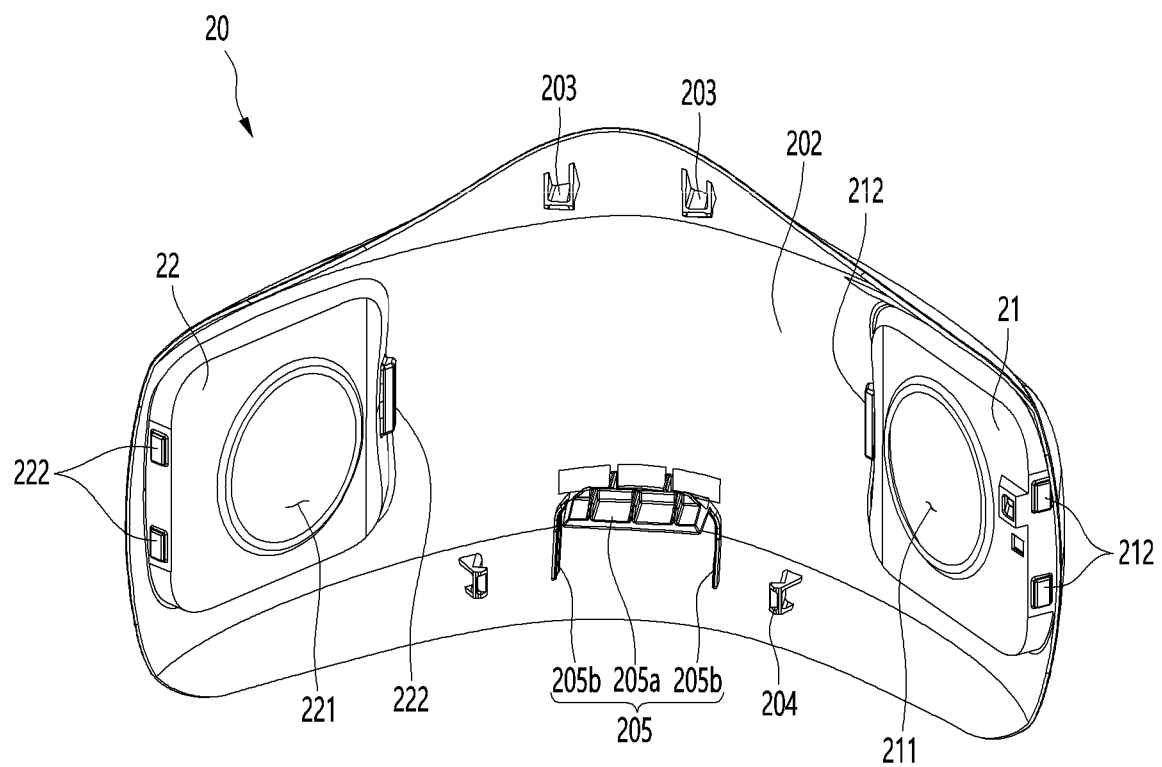
FIG. 9 is a rear perspective view showing the mask body cover.

FIG. 8 is a front perspective view of the mask body cover, and FIG. 9 is a rear perspective view of the mask body cover.

Referring to FIGS. 8 and 9, the mask body cover 20 can be coupled to the front of the mask body 10. The mask body cover can extend in the left and right direction, and a center portion of the mask body cover 20 can be convexly rounded forward. Also, the mask body cover 20 can be provided to be symmetrical to each other in the left and right direction with respect to a vertical surface passing through a center of the front surface thereof.

The mask body cover 20 can include a cover front surface 201 defining an outer surface or a front surface thereof, and a cover rear surface 202 defining an inner surface or a rear surface thereof.

The cover front surface 201 can be a portion that is exposed to the outside to define an outer appearance thereof when the user wears the mask apparatus 1. The cover front surface 201 can include a first filter mounting portion 21 on which the first filter 23 is mounted and a second filter mounting portion 22 on which the second filter 24 is mounted.

The first filter mounting portion 21 and the second filter mounting portion 22 can be provided to be symmetrical to each other in the left and right direction with respect to the center of the front surface 201 of the cover. The first filter mounting portion 21 and the second filter mounting portion 22 can have the same or similar shape to each other.

In some implementations, the first filter mounting portion 21 and the second filter mounting portion 22 can be provided by partially recessing the front surface 201 of the cover. For example, in the first filter mounting portion 21 and the second filter mounting portion 22, a portion of the front surface 201 of the cover can be recessed backward to define a space in which the first filter 23 and the second filter 24 are seated.

In some examples, each of the first filter mounting portion 21 and the second filter mounting portion 22 can have a bottom surface, on which the first filter 23 and the second filter 24 contact and are supported, and a plurality of side surfaces defining edges of the bottom surface.

A first air suction hole 211 through which external air is suctioned may be defined in the bottom surface of the first filter mounting portion 21. The air passing through the first filter 23 can be suctioned into the first fan module 16 through the first air suction hole 211.

The first air suction hole 211 can be disposed at a center of the bottom surface. For example, the first air suction hole 211 can be provided to be opened in a circular shape.

At least one or more first filter cover mounting grooves 212 for mounting the first filter cover 25 can be defined in the side surfaces of the first filter mounting portion 21.

The first filter cover mounting groove 212 can be defined by being further recessed inward from the side surface of the first filter mounting portion 21. Thus, the coupling protrusion 262 protruding from the edge of the first filter cover 25 can be fitted and coupled to the first filter cover mounting groove 212 and then be mounted on the first filter mounting portion 21.

In some implementations, the first filter cover mounting groove 212 can be defined in each of two side surfaces of the first filter mounting portion 21 facing each other, among the side surfaces of the first filter mounting portion 21. In detail, the first filter cover mounting groove 212 can include one or a plurality of mounting grooves defined in one of the two side surfaces facing each other and one or a plurality of mounting grooves defined in the other of the two side surfaces.

Also, at least one of the side surfaces of the first filter mounting portion 21, i.e., one of the two side surfaces, in which the first filter cover mounting groove is defined, can be provided to be inclined. For example, among the side surfaces of the first filter mounting portion 21, the side surface adjacent to a front center of the mask body cover 20 can be provided to be gradually inclined in a direction that is close to the front center of the mask body cover 20, as it goes from the rear surface of the mask body cover 20 towards the front surface of the mask body cover 20.

The reason in which at least one of the side surfaces of the first filter mounting portion 21 is provided to be inclined is to facilitate attachment/detachment of the first filter cover 25. That is, when the side surface in which the first filter cover mounting groove 212 is defined is provided to be inclined, in a state in which the coupling protrusion 262 protruding from one side end of the first filter cover 25 is inserted into the first filter cover mounting groove 212, the coupling protrusion 262 protruding from the other side end of the first filter cover 25 can be inserted into the first cover mounting groove 212 that is defined in the inclined surface, while the other side end of the first filter cover 25 is slid along the inclined side surface.

Likewise, a second air suction hole 221 through which external air is suctioned can be defined in the bottom surface of the second filter mounting portion 22. The air passing through the second filter 24 can be suctioned into the second fan module 17 through the second air suction hole 221.

The second air suction hole 221 can be disposed at a center of the bottom surface. For example, the second air suction hole 221 can be provided to be opened in a circular shape.

At least one or more second filter cover mounting grooves 222 for mounting the second filter cover 26 can be defined in side surfaces of the second filter mounting portion 22.

Since the second filter mounting portion 22 has a shape that is symmetrical to the shape of the first filter mounting portion 21, duplicated descriptions of the second filter mounting portion 22 will be omitted.

The cover rear surface 202 is coupled to cover the entire surface of the mask body 10 and serves to protect a plurality of components mounted on the mask body 10.

A plurality of coupling ribs for coupling to the mask body 10 can be disposed on the rear surface 202 of the cover. The plurality of coupling ribs can be provided to protrude backward from the cover rear surface 202.

The plurality of coupling ribs can include a first coupling rib 203 provided at an upper portion of the cover rear surface 202 and a second coupling rib 204 provided at a lower portion the cover rear surface 202.

The second coupling rib 204 can be fitted and coupled to the second cover coupling portion 106 provided on the mask body 10. The second coupling ribs 204 can be plurality in plurality so as to be spaced apart from an upper portion of the cover rear surface 202 to both sides.

In this case, an interval between the plurality of second coupling ribs 204 can be greater than that between the plurality of first coupling ribs 203.

The plurality of coupling ribs can further include a third coupling rib 205 provided at a lower portion of the cover rear surface 202. The third coupling rib 205 can be fitted and coupled to the air discharge portion 150 provided in the mask body 10. The third coupling rib 205 can be provided between the plurality of second coupling ribs 204.

The third coupling rib 205 includes a horizontal rib 205*a* protruding horizontally backward from the cover rear surface 202 and vertical ribs 205*b* extending downward from both sides of the horizontal rib 205*a*.

Here, the air discharge portion 150 can be coupled to surround outer edges of the horizontal rib 205*a* and the vertical ribs 205*b*. In detail, at least a portion of the third coupling rib 205 can be coupled in close contact with the inner side of the air discharge portion 150. Thus, bonding force between the mask body 10 and the mask body cover 20 can be further improved.

Figure 10:
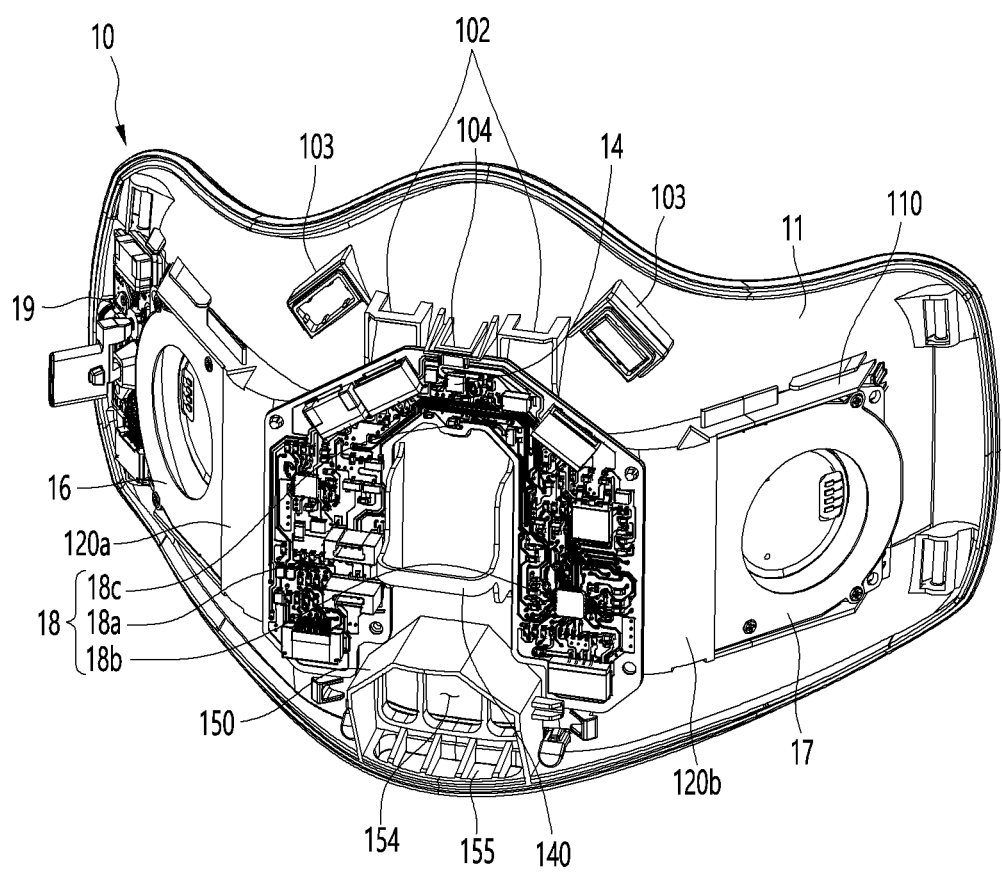
FIG. 10 is a front perspective view showing the mask apparatus in a state in which the mask body cover and a battery are removed from the mask apparatus.
Figure 11:
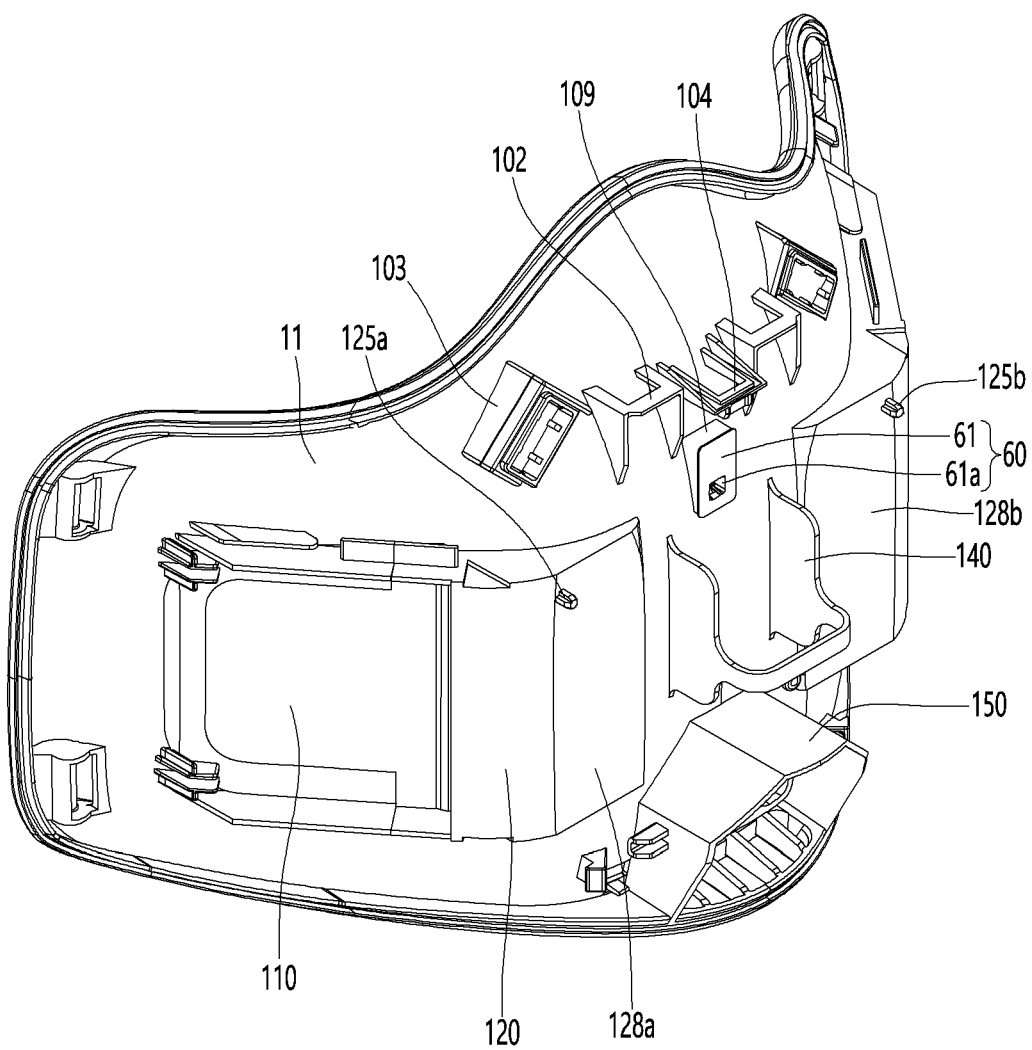
FIG. 11 is a view illustrating showing an example of a control module that is separated from the mask body.
Figure 12:
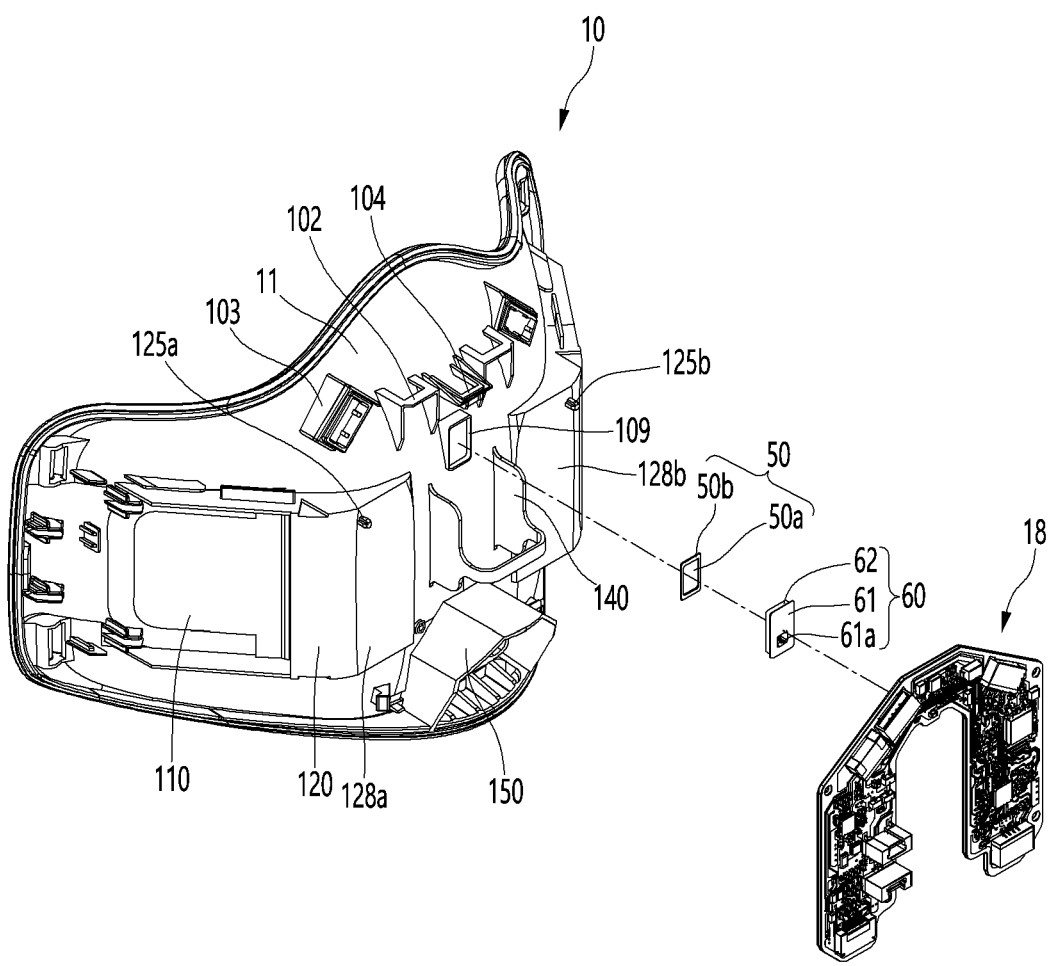
FIG. 12 is an exploded perspective view showing the mask body of FIG. 10.

FIG. 10 is a front perspective view showing the mask apparatus in a state in which the mask body cover and a battery are removed from the mask apparatus, FIG. 11 is a view illustrating an example of a control module that is separated from the mask body, FIG. 12 is an exploded perspective view showing the mask body of FIG. 10, and FIG. 13 is a rear perspective view showing the mask body.

Referring to FIGS. 10 to 13, the mask apparatus 1 includes a mask body 10 on which a plurality of electronic components are installed, and a mask body cover 20 detachably coupled to the mask body 10. The mask body cover 20 can cover the plurality of electronic components mounted on the mask body 10 to prevent the plurality of electronic components from being exposed to the outside.

When the mask body cover 20 is separated from the mask body 10, the entire surface of the mask body 10 can be exposed as illustrated in FIG. 10.

The mask body 10 can be coupled to the rear of the mask body cover 20. The mask body 10 can be provided to extend in the left and right direction, and a center portion of the mask body 10 can be convexly rounded forward. Also, like the mask body cover 20, the mask body 10 can be provided symmetrically in a horizontal direction with respect to the vertical surface passing through the center. That is, the mask body 10 can have a shape and size corresponding to the mask body cover 20.

The mask body 10 can include a body front surface 11 coupled to the mask body cover 20 and a body rear surface 12 coupled to the sealing bracket 30 or the seal 40.

The body front surface 11 defines a space in which the plurality of electronic components are installed, and a plurality of structures coupled with the mask body cover 20 are provided.

Particularly, a battery 13 is disposed at the center of the body front surface 11. The battery 13 can supply power to at least one of the control module 18, the power module 19, or the fan modules 16 and 17.

The battery 13 can have sufficient capacity to enable high-speed rotation of the fan modules 16 and 17. For example, two batteries, each of which has a capacity of 400 mAh, can be connected to each other in series. Alternatively, the battery 13 can be provided with one large-capacity battery.

The battery 13 can be relatively heavy among the electronic components. Thus, the battery 13 can be disposed at a central portion of the mask body 10 hung on the user's nose. According to this configuration, since the battery 13 is disposed at the center of the mask apparatus 1, the user can feel less load on his/her ears when wearing the mask apparatus 1, when compared to a case in which the battery 13 is disposed at the side edge of the mask body 10.

Also, since the battery 13 is disposed at the center of the mask body 10, power can be easily provided to all of the control module 18, the power module 19, and the fan modules 16 and 17. That is, there is an advantage of being able to easily connect wires to various electronic components that require power.

For this, a battery mounting portion 140 supporting the battery 13 is disposed at the central portion of the body front surface 11. The battery mounting portion 140 can have a rib shape protruding forward from the body front surface 11.

In some implementations, the battery mounting portion 140 can include a pair of vertical ribs 141 disposed to extend in the vertical direction on the body front surface 11 and a horizontal rib 142 connecting the pair of vertical ribs 141 to each other.

The pair of vertical ribs 141 can be provided to be spaced apart from each other in the left and right direction so as to be symmetrical to each other with respect to the center of the body front surface 11. Also, each front end of the pair of vertical ribs 141 can be bent in a direction facing each other to provide the horizontal ribs 142. Thus, the pair of vertical ribs 141 and horizontal ribs 142 can define a battery accommodation space 143 in which the battery 13 is accommodated.

When the battery 13 is accommodated in the accommodation space 143, a front surface of the battery 13 can be supported by the horizontal ribs 142, and a side surface of the battery 13 can be supported by the vertical ribs 141. Also, a lower end of the battery 13 can be supported by an upper end of the air discharge portion 150. According to this configuration, the battery 13 can be prevented from being removed from the battery mounting portion 140, and the battery 13 can be stably supported.

In some implementations, a control module 18 is disposed at a center of the body front surface 11. The control module 18 can be electrically connected to the power module 19, the fan modules 16 and 17, and the battery 13. The control module 18 can be seated on the front surface of the air duct 120 through which air suctioned from the fan modules 16 and 17 flows and can be cooled by air flowing along the air duct 120. That is, heat generated in the control module 18 can be transferred to the air flowing along the air duct 120 through heat conduction between the front surface of the air duct 120 and the control module 18.

In some examples, the control module 18 can include a controller, an electric circuit, one or more processors, or the like, that can control operation of components of the mask apparatus 1 such as the pressure sensor 14 and the fan modules 16 and 17.

The control module 18 can be disposed to surround the battery 13. Here, the central portion of the control module 18 can be opened, and the battery 13 can be disposed at the opened center of the control module 18.

The control module 18 can have an n-shape with an opened central portion to avoid an interference with the battery 13. For example, the control module 18 can be provided as an n-shaped single substrate, or a plurality of substrates 18a, 18b, and 18c can be connected to each other to define the n-shape.

Particularly, the substrate constituting the control module 18 can include a first substrate 18a disposed at a right side and a second substrate 18b disposed on at left side with respect to the body front surface 11, the substrate constituting the control module 18 can further include a third substrate 18c connecting the first substrate 18a to the second substrate 18b. The first substrate 18a, the second substrate 18b, and the third substrate 18c can be integrated with each other.

The first substrate 18a can be disposed at a right side of the battery 13, the second substrate 18b can be disposed at a left side of the battery 13, and the third substrate 18c can be disposed above the battery 13. The third substrate 18c can be disposed to avoid overlapping with the battery 13. Thus, the battery 13 and the control module 18 can be efficiently and densely disposed within a limited space.

Control module mounting portions 128a and 128b on which the control module 18 is mounted are disposed on the body front surface 11. The control module mounting portions 128a and 128b can be provided so that a portion of the front surface of the air duct 120 is provided in a plane.

Coupling portions 125a and 125b for coupling the substrates 18a, 18b, and 18c of the control module 18 are disposed on the control module mounting portions 128a and 128b. The plurality of coupling portions 125a and 125b can be disposed on the first control module mounting portion 128a and the second control module mounting portion 128b, respectively.

As an example, the plurality of coupling portions 125a, 125b pass through portions of edges of the substrates 18a, 18b, 18c, respectively, so that the control module 18 is fixed to the control module mounting portions 128a, 128b. Alternatively, a separate coupling member can pass through the substrates 18a, 18b, and 18c to be coupled to the control module mounting portions 128a and 128b.

In some examples, the first substrate 18a can be disposed on the first control module mounting portion 128a of the air duct 120, and the second substrate 18b can be disposed on the second control module mounting portion 128b of the air duct 120, and the third substrate 18c can be disposed above the air duct 120. Thus, the air suctioned from the first fan module 16 and the second fan module 17 can pass through the air duct 120 to cool the first substrate 18a, the second substrate 18b, and the third substrate 18c.

The mask apparatus 1 further includes a pressure sensor 14. The pressure sensor 14 can be disposed on a sensor mounting portion 109 disposed on the body front surface 11 to sense a pressure of the breathing space S.

The pressure sensor 14 can be installed on the substrate of the control module 18 to be disposed in an installation space defined inside the sensor mounting portion 109. For example, the pressure sensor 14 can be installed on the third substrate 18c to protrude to the rear of the third substrate 18c. For this, the third substrate 18c can be disposed in front of the sensor mounting portion 109.

When the pressure sensor 14 is disposed in the installation space of the sensor mounting portion 109, information of the breathing space can be obtained from air introduced into the installation space through a hole communicating with the installation space and the breathing space.

Pressure information or breathing information sensed by the pressure sensor 14 can be provided to the control module 18, and operations of the fan modules 16 and 17 can be controlled based on the pressure information and breathing information.

The sensor mounting portion 109 can have a rectangular shape of which the inside is empty, but is not limited thereto.

As an example, the sensor mounting portion 109 can include a first portion 109a that protrudes forward from the front surface of the mask body 10, that has a predetermined width, and that extends in a direction parallel to the ground. The sensor mounting portion 109 can further include a pair of second portions 109b extending downward from each of both sides of the first portion 109a, and a third portion 109c connecting ends of the pair of second portions 109b to each other.

The first portion 109a can define a top surface of the sensor mounting portion 109, the second portion 109b can define both side surfaces of the sensor mounting portion 109, and the third portion 109c can define a bottom surface of the sensor mounting portion 109.

The first fan module 16 and the second fan module 17 are disposed on both sides of the body front surface 11, respectively. The first fan module 16 can be disposed at a right side of the control module 18, and the second fan module 17 can be disposed at a left side of the control module 18.

The first fan module 16 is mounted on a first fan module mounting portion 110a disposed at the right side of the body front surface 11, and the second fan module 17 is mounted on a second fan module mounting portion 110b disposed at the left side of the body front surface 11. The first fan module 16 and the second fan module 17 can be disposed to be symmetrical to each other in the left and right direction with respect to the center of the mask body 10.

The power module 19 can be disposed on the edge of the body front surface 11. The power module 19 can receive power from a power source to perform a function of turning on or off the power of the mask apparatus 1. The power module 19 can be disposed on a side of any one of the first fan module 16 and the second fan module 17. That is, the power module 19 can be disposed on a left edge or a right edge of the body front surface 11.

A power module mounting portion 130 for mounting the power module 19 is disposed on the body front surface 11. The power module mounting portion 130 can include a plurality of ribs, which are disposed on the left edge or the right edge of the body front surface 11 to support the power module 19.

The battery 13, the control module 18, the fan modules 16 and 17, and the power module 19 can be arranged in a line in a widthwise direction of the mask body 10.

The mask apparatus 1 further includes a waterproof film 50 disposed inside the sensor mounting portion 109. The waterproof film 50 can be provided as a porous thin film. The waterproof film 50 can have a circular or polygonal shape.

The waterproof film 50 can be provided between the mask body 10 and the pressure sensor 14 to prevent moisture or foreign substances introduced from the breathing space from moving toward the pressure sensor 14.

The waterproof film 50 prevents moisture or foreign substances from being accumulated in the pressure sensor 14 by allowing air introduced from the breathing space to pass through and blocking the moisture or foreign substances introduced from the breathing space. Accordingly, the pressure sensor 14 can be prevented from failing due to the permeation of the moisture, etc., and the pressure sensor 14 can accurately measure a pressure in the breathing space.

In some implementations, the waterproof film 50 can be provided with a plurality of fine holes so that only air passes through the fine holes. At least a portion of the waterproof film 50 can be made of a porous material. The waterproof film 50 can include an edge portion 50b and a porous film 50a disposed inside the edge portion.

For example, the waterproof film 50 can be made of a Gore-Tex material. That is, the waterproof film 50 can be provided as a fluorine resin film having fine holes.

Alternatively, the waterproof film 50 can be made of an organic porous material. The waterproof film 50 can be made of a membrane material.

The mask apparatus 1 further includes a sensor sealing member 60 coupled to the sensor mounting portion 109. The sensor sealing member 60 is coupled to the inside of the sensor mounting portion 109 to serve to pressurize the waterproof film 50. In addition, the sensor sealing member 60 serves to shield an opening surface defined in the front end of the sensor mounting portion 109. The sensor sealing member 60 can be provided as a plastic injection product.

The sensor sealing member 60 can be disposed between the waterproof film 50 and the control module 18. A rear surface of the sensor sealing member 60 can be in close contact with a front surface of the waterproof film 50, and the front surface can be in close contact with a rear surface of the control module 18. The sensor sealing member 60 can be pressed by the control module 18 to press the waterproof film 50. In some examples, when the control module 18 is installed on the mask body 10, a hook portion of the support rib 104 can press an upper end of the front surface of the control module 18 backward. Accordingly, the control module 18, the sensor sealing member 60, and the waterproof film 50 can be sequentially pressed. As a result, there is an advantage that the waterproof film 50 is firmly supported on the inside of the sensor mounting portion 109 without being shaken.

Figure 14:
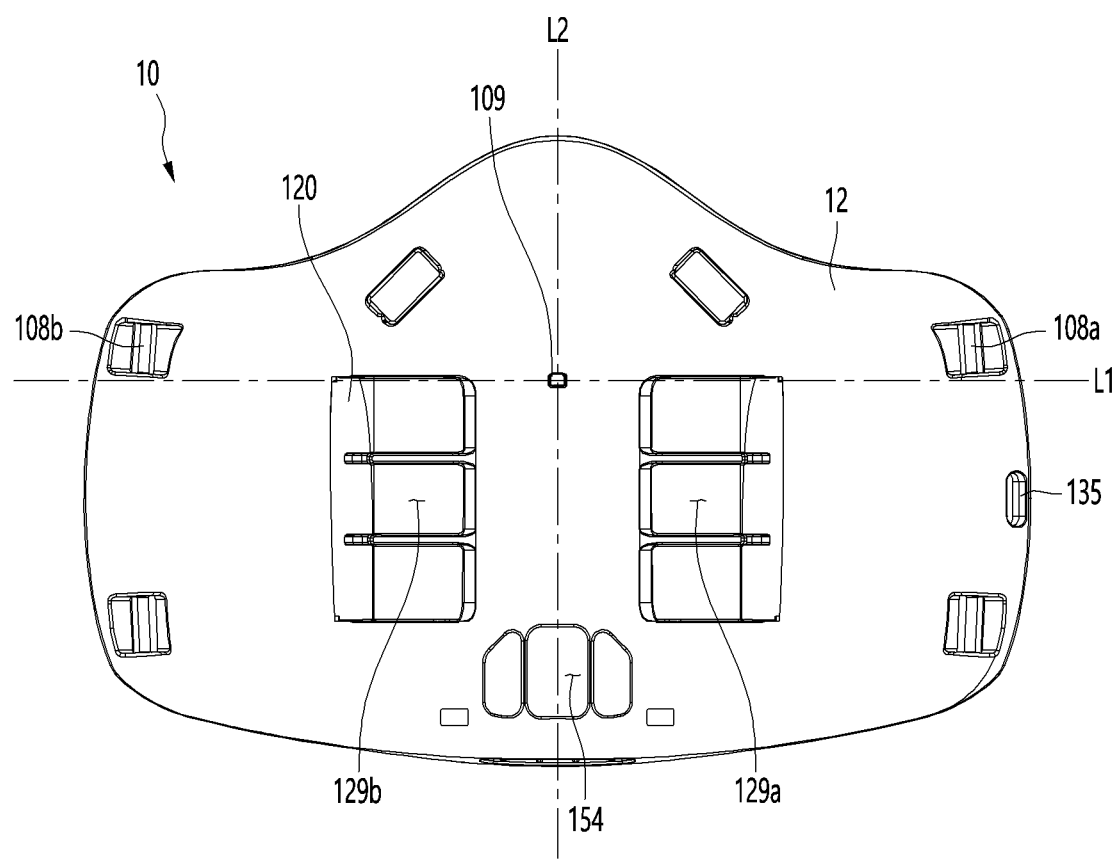
FIG. 14 is a rear view showing the mask apparatus.
Figure 15:
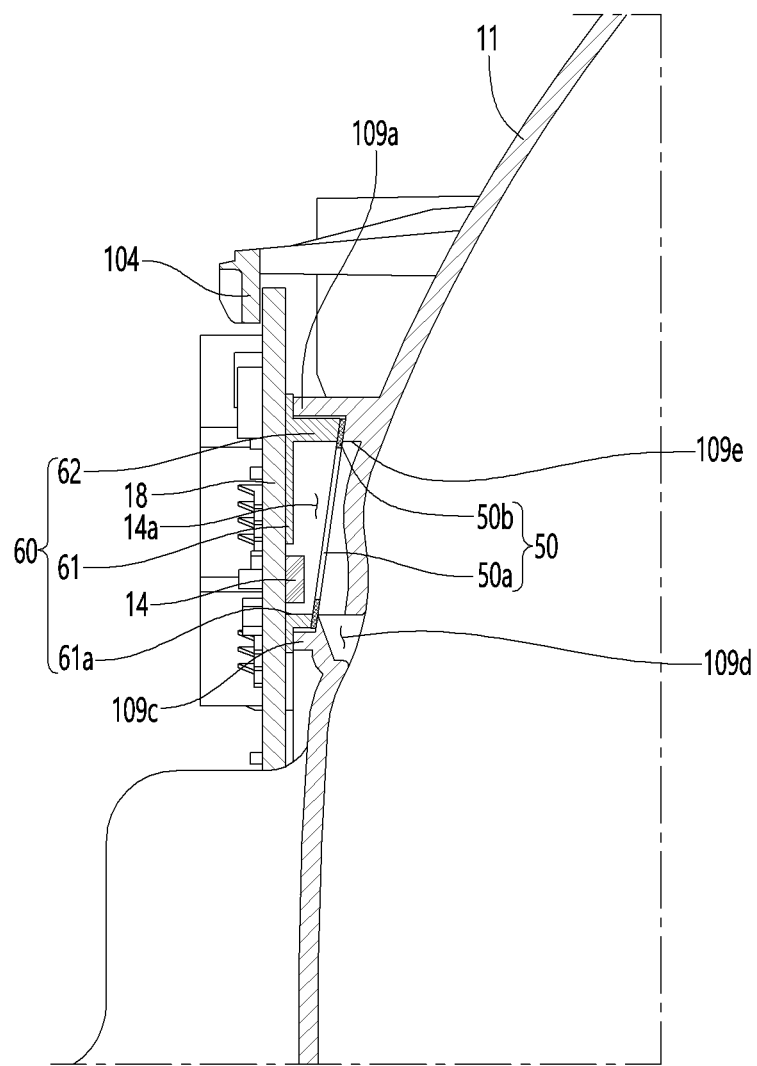
FIG. 15 is a cross-sectional view illustrating an example of a pressure sensor.
Figure 16:
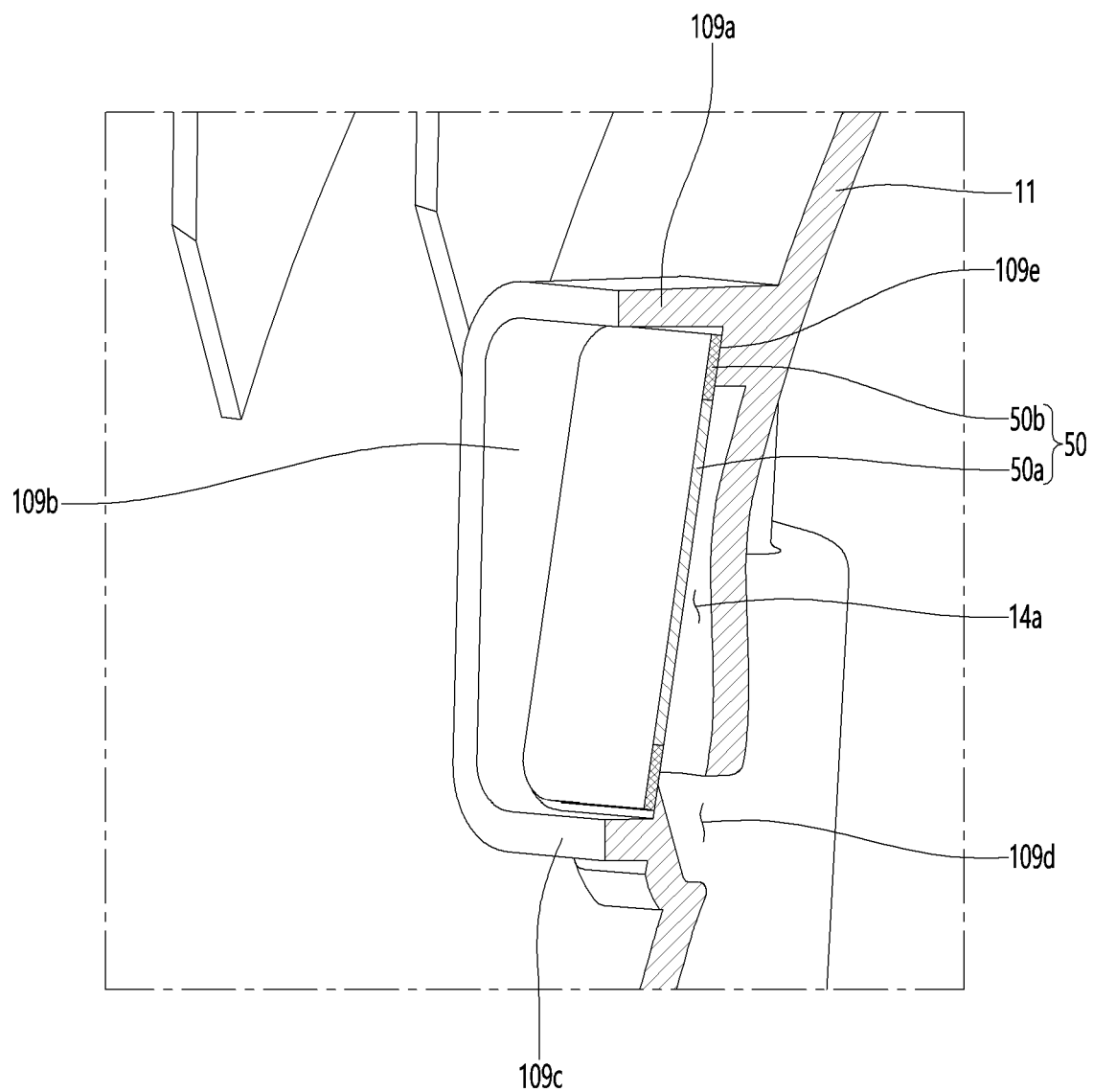
FIG. 16 is a cross-sectional view illustrating an example of a sensor mounting portion.
Figure 17:
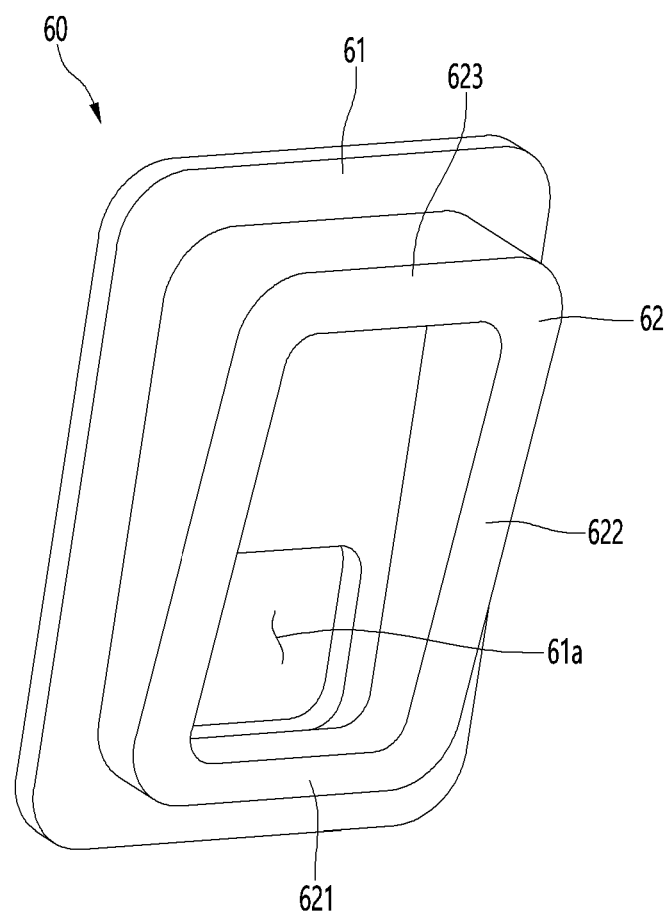
FIG. 17 is a perspective view illustrating an example of a sensor sealing member.

FIG. 14 is a rear view illustrating the mask apparatus, FIG. 15 is a cross-sectional view illustrating an example of an assembly structure of the pressure sensor, FIG. 16 is a cross-sectional view illustrating an example of the sensor mounting portion, and FIG. 17 is a perspective view illustrating an example of a sensor sealing member.

Referring to FIGS. 14 to 17, the pressure sensor 14 can be mounted on a sensor mounting portion 109 disposed on the front surface of the mask body 10. At least a portion of the pressure sensor 14 can be disposed in an installation space 14a defined inside the sensor mounting portion 109 to sense a pressure of the breathing space.

Here, the pressure of the breathing space can be understood as an inner pressure of the mask apparatus.

At least a portion of the installation space 14a can be defined through the mask body 10. Also, one surface (front surface) of the installation space 14a can be opened to accommodate the pressure sensor 14, and the other surface (rear or bottom surface) can be opened to communicate with the breathing space S.

The pressure sensor 14 can be an air pressure sensor that measures a pressure or air pressure in a sealed space using a flow rate or wind strength of introduced air. Alternatively, the pressure sensor 14 can be a differential pressure sensor that measures a pressure change in a sealed space. Since the pressure sensor 14 is the well-known technology, a detailed description thereof will be omitted.

In some implementations, a communication hole 109*d* connecting the installation space 14*a* of the sensor mounting portion 109 to the breathing space can be defined in the other surface of the sensor mounting portion 109.

The communication hole 109*d* can be defined by passing through the mask body 10 so as to connect the installation space 14*a* of the sensor mounting portion 109 to the breathing space. Also, the sensor mounting portion 109 can be disposed in such a manner in which the ribs protrude along the communication hole 109*d* or the edge of the installation space 14*a*.

The communication hole 109*d* can be defined by cutting a portion of the mask body 10. Thus, a portion of the air discharged to the breathing space can be introduced into the installation space 14*a*, in which the pressure sensor 14 is disposed, through the communication hole 109*d*.

When the mask apparatus 1 is worn, the communication hole 109*d* can be disposed adjacent to the user's nose or mouth. For example, the communication hole 109*d* can be designed to be placed at a point facing a user's philtrum.

Since the pressure sensor 14 is disposed at the position adjacent to the user's nose or mouth, it is possible to accurately sense a pressure change caused by air exhaled from the nose or mouth.

If the communication hole 109*d* or the pressure sensor 14 is disposed at a too high or too low position with respect to the user's nose or mouth, there is a limitation in that the pressure change due to the exhaled air is not accurately sensed. For example, the communication hole 109*d* or the pressure sensor 14 can be disposed at a point (facing) corresponding to or facing the philtrum between the nose and the mouth of the user.

For example, the communication hole 109*d* can be disposed at an intermediate point between the first air outlet 129*a* and the second air outlet 129*b* provided in the rear surface of the mask body 10. Particularly, the communication hole 109*d* can be disposed at a point corresponding to a first reference line L1 connecting upper ends of the first air outlet 129*a* and the second air outlet 129*b* to each other.

Also, the communication hole 109*d* can be disposed at a point corresponding to a vertical second reference line L2 that equally divides the mask body 10 horizontally. The communication hole 109*d* can be disposed at a point at which the first reference line L1 and the second reference line L2 meet each other. For example, the communication hole 109*d* can be defined at an intersection of the first reference line L1 and the second reference line L2.

The communication hole 109*d* can be defined at a point lower than a height of the sensor mounting portion 109. That is, the communication hole 109*d* can be connected to a lower portion of the installation space 14*a* of the sensor mounting portion 109 so that the air discharged to the breathing space is prevented from directly flowing into the pressure sensor 14.

If, when breathing and snorting from the user's mouth or nose directly flows into the pressure sensor 14, water vapor contained in the breath and snort can be in direct contact with the pressure sensor 14 to cause fogging.

When the fogging occurs on the pressure sensor 14, an ambient humidity of the pressure sensor 14 can increase, and as a result, moisture can be permeated into the pressure sensor 14 to deteriorate reliability of the sensor.

In some examples, the pressure sensor 14 can be disposed at a point higher than the communication hole 109*d* so that the breathing and snorting is not directly directed to the pressure sensor 14 when the user breathes. As a result, the air exhaled by the user can flow upward along the communication hole 109*d* to reach the pressure sensor 14.

Also, since an air passage from the breathing space of the mask toward the pressure sensor 14 is provided upward from a lower side, a phenomenon in which moisture or saliva contained in the air from the user's mouth or nose can flow into the pressure sensor 14 can be minimized to prevent the pressure sensor 14 from being contaminated or wetted.

Here, the installation space 14*a* of the sensor mounting portion 109 and the communication hole 109*d* can be referred to as an "opening."

In addition, the installation space 14*a* can be referred to as a "first space," and the communication hole 109*d* can be referred to as a "second space." That is, the first space can be understood as a space in which the pressure sensor 14 is disposed, and the second space can be understood as a passage connecting the first space to the breathing space. The first space is disposed at a point higher than the second space.

The rear surface (or bottom surface) of the sensor mounting portion 109 can face the pressure sensor 14, and a portion of the rear surface can be cut to define the communication hole 109*d*.

Each of the first portion 109*a*, the second portion 109*b*, and the third portion 109*c* can protrude forward from the front surface of the mask body 10. Here, lengths of the first portion 109*a*, the second portion 109*b*, and the third portion 109*c*, which protrude forward, can be the same, but are not limited thereto.

Thus, when the control module 18 is installed on the mask body 10, the rear surface of the control module 18 can be seated on a front end of each of the first portion 109*a*, the second portion 109*b*, and the third portion 109*c*, and thus, the opened front surface of the sensor mounting portion 109 can be completely shielded by the control module 18. Here, the pressure sensor 14 mounted on the rear surface of the control module 18 can be disposed in the installation space 14*a* of the sensor mounting portion 109.

In addition, when the control module 18 is installed on the sensor mounting portion 109 so that the pressure sensor 14 is disposed, the pressure sensor 14 can be covered by the sensor mounting portion 109. Also, the pressure sensor 14 can be disposed adjacent to the communication hole 109*d*, and thus, it can be possible to acquire information of the breathing space from the air introduced into the installation space 14*a* through the communication hole 109*d*.

To minimize an influence of wind discharged from the fan modules 16 and 17 on the pressure sensor 14, the pressure sensor 14 can be disposed to be as far apart as possible from the fan modules 16 and 17.

The reason in which the pressure sensor 14 is maximally spaced apart from the discharge hole of the fan modules 16 and 17 is before a flow speed of air suctioned by the fan modules 16 and 17 is high. In detail, when the pressure sensor 14 is installed at the position that is close to the discharge hole of the fan modules 16 and 17, it is difficult to allow the pressure sensor 14 to accurately measure the air pressure inside the suction space S. Thus, the pressure sensor 14 can be disposed at the intermediate point between the first fan module 16 and the second fan module 17.

The pressure sensor 14 can be disposed at the intermediate point between the first air outlet 129a and the second air outlet 129b, which are provided in the rear surface of the mask body 10.

Particularly, like the communication hole 109d, the pressure sensor 14 can be disposed on an area corresponding to the first reference line L1 connecting the upper ends of the first air outlet 129a and the second air outlet 129b to each other.

Also, the pressure sensor 14 can be disposed on an area corresponding to a vertical second reference line L2 that equally divides the mask body 10 horizontally. The pressure sensor 14 can be disposed on an area on which the first reference line L1 and the second reference line L2 meet each other.

That is, the pressure sensor 14 can be disposed at a point that is spaced a predetermined distance upward from the center of the mask apparatus 1. Here, when the user wears the mask apparatus 1, the pressure sensor 14 can be disposed at a portion adjacent to the user's nose.

According to this configuration, since the pressure sensor 14 is maximally spaced apart from the fan modules 16 and and is disposed adjacent to the user's nose, the pressure inside the mask (pressure of the breathing space) according to the user's breathing state can be accurately sensed.

At least a portion of the sensor mounting portion 109 can be inclined. For example, the third portion 109c can be inclined toward the inside of the installation space 14a.

Particularly, the third portion 109c can extend to be inclined upward from the front surface of the mask body 10. Particularly, when the third portion 109c extends to be inclined upward, a cross-sectional area (width) of the passage of the communication hole 109d connecting the installation space 14a of the sensor mounting portion 109 to the breathing space can be narrowed. When the cross-sectional area of the passage of the communication hole 109d is narrowed, a direct flow of air from the user's nose to the pressure sensor 14 can be minimized to more improve sensing accuracy of the pressure sensor 14.

In some examples, where a portion of the sensor mounting portion 109 is inclined, the passage of the communication hole 109d can be inclined. That is, a flow direction of the air introduced to the pressure sensor 14 can be changed to prevent the air discharged the nose from being directly introduced into the pressure sensor 14.

A waterproof film 50 is disposed inside the sensor mounting portion 109.

The waterproof film 50 can be seated on a seating surface 109e formed inside the sensor mounting portion 109. The seating surface 109e can protrude in a stepped shape along an inner edge of the sensor mounting portion 109. In addition, an edge portion 50b of the waterproof film 50 can be supported on the seating surface 109e. The waterproof film 50 can be inserted in a state where an upper portion thereof is inclined backward.

The sensor sealing member 60 can be coupled to the inside of the sensor mounting portion 109 to press the waterproof film 50. In addition, the sensor sealing member 60 can cover the opened portion of the sensor mounting portion 109. The sensor sealing member 60 can be disposed between the front end of the sensor mounting portion 109 and the control module 18. Also, the sensor sealing member 60 can be disposed between the control module 18 and the sensor mounting portion 109. In some implementations, the sensor sealing member can include a plate or a bracket including a protrusion and an opening.

The sensor sealing member 60 can block moisture or foreign substances introduced from the breathing space. For example, the sensor sealing member 60 can block moisture or foreign substances moving to the pressure sensor 14 or the control module 18. In some examples, the sensor sealing member can be made of silicone or a waterproof material having elasticity. In some cases, the sensor sealing member 60 can be injection-molded to form a single body.

The sensor sealing member 60 can be disposed between the waterproof film 50 and the control module 18. An outer surface of the sensor sealing member 60 can be in close contact with the inner surface of the sensor mounting portion 109. Accordingly, even if the moisture is introduced between the waterproof film 50 and the seating surface 109e of the sensor mounting portion 109, leakage of the moisture to the control module 18 or the pressure sensor 14 can be prevented.

For example, the sensor sealing member 60 can include a cover portion 61 that covers the opened surface of the sensor mounting portion 109 and an extension portion 62 extending from the cover portion 61 and inserted into the sensor mounting portion 109.

The cover portion 61 can have a plate shape having a size corresponding to that of the sensor mounting portion 109. In addition, a sensor opening 61a through which the pressure sensor 14 fixed to the control module 18 passes can be defined in one side of the cover portion 61.

The sensor opening 61a can be defined in a lower portion of the cover portion 61. The sensor opening 61a can have a square shape, but is not limited thereto.

The extension portion 62 is inserted into the sensor mounting portion 109 to serve to press the waterproof film 50. The extension portion 62 protrudes backward from the cover portion 61. For example, the extension portion 62 can protrude from a portion of the rear surface of the cover portion 61 to form a closed curve. Here, the extension portion 62 can protrude backward from the inside so as to have a cross-sectional area less than that of the cover portion 61. That is, the extension portion 62 can extend from the rear surface of the cover portion 61 and can be disposed at a point spaced inward from the edge of the cover portion 61.

In some implementations, the extension portion 62 can include a lower end 621 extending in a horizontal direction from a lower portion of the cover portion 61, a pair of side ends extending upward from both sides of the lower end 621, and an upper end connecting the pair of side ends 622 to each other.

The upper end 623 can extend longer than a protruding length of the lower end 621. In addition, a length of the upper end of each of the pair of side ends 622 can be longer than that of the lower end. That is, an end of the extension portion 62 can be provided to be inclined backward from a lower side to an upper side.

Due to this configuration, when the sensor sealing member 60 is inserted into the sensor mounting portion 109, each of ends 621, 622, and 623 of the extension portion 62 can press a front surface of the edge portion 50b of the waterproof film 50 disposed inside the sensor mounting portion 109. Also, the cover portion 61 can be seated on the front end of the sensor mounting portion 109 to cover the opened front surface of the sensor mounting portion 109.

When the control module 18 is installed on the mask body 10, the upper end of the front surface of the control module 18 can be pressed backward by the support rib 104, and the front surface of the sensor sealing member 60 can be in close contact with the control module 18.

Also, when the control module 18 is caught on the support rib 104 and coupled to the front surface of the mask body 10, the pressure sensor 14 can be disposed in the sensor opening 61a of the cover portion 61.

Accordingly, the control module 18, the sensor sealing member 60, and the waterproof film 50 can be sequentially pressed. In this case, there is an advantage that the waterproof film 50 is firmly supported on the inside of the sensor mounting portion 109 without being shaken.

What is claimed is:

1. A mask apparatus comprising:
a mask body that defines a communication hole;
a sensor mounting portion that extends from a front surface of the mask body and surrounds the communication hole, the sensor mounting portion defining an installation space therein;
a seal coupled to a rear surface of the mask body and configured to define a breathing space between the mask body and a user;
a pressure sensor accommodated in the installation space and configured to sense air pressure inside the breathing space that is in communication with the communication hole;
a film disposed in the installation space and configured to restrict permeation of moisture from the breathing space into the installation space through the communication hole; and
a sensor sealing member configured to apply pressure to the film,
wherein the sensor sealing member comprises:
a cover portion that covers an opening defined at a front surface of the sensor mounting portion, and
an extension portion that extends from a rear surface of the cover portion and is configured to apply pressure to the film, and
wherein the pressure sensor and the film are directly adjacent to each other in the installation space.

2. The mask apparatus according to claim 1, further comprising:
a pair of fan modules mounted at a left side and a right side of the front surface of the mask body, respectively; and
a pair of air ducts disposed on the front surface of the mask body, each of the pair of air ducts being disposed at an outlet side of one of the pair of fan modules,
wherein the mask body defines a plurality of air outlets in the rear surface of the mask body, the plurality of air outlets being in communication with the outlet sides of the pair of air ducts.

3. The mask apparatus according to claim 2, wherein the communication hole is defined at a position in a vertical line that bisects the mask body into left and right sides.

4. The mask apparatus according to claim 3, wherein the plurality of air outlets comprise a pair of air outlets that are spaced apart from each other in a horizontal direction, and
wherein the communication hole is defined at an intersection between the vertical line and a horizontal line that passes through upper ends of the pair of air outlets.

5. The mask apparatus according to claim 2, wherein the plurality of air outlets comprise a pair of air outlets that are spaced apart from each other in a horizontal direction, and
wherein the communication hole is defined at a position in a horizontal line that passes through upper ends of the pair of air outlets.

6. The mask apparatus according to claim 2, wherein the plurality of air outlets comprise a pair of air outlets that are defined in the breathing space.

7. The mask apparatus according to claim 1, wherein the film comprises a porous film.

8. The mask apparatus according to claim 7, wherein the film further comprises an edge portion disposed along an edge of the porous film.

9. The mask apparatus according to claim 8, wherein the sensor mounting portion comprises a seating surface that is disposed at an inside of the sensor mounting portion and supports the edge portion of the film.

10. The mask apparatus according to claim 1, wherein the sensor mounting portion comprises:
a first portion that extends forward from the front surface of the mask body;
a pair of second portions that extend downward from ends of the first portion; and
a third portion that connects lower ends of the pair of second portions to each other.

11. The mask apparatus according to claim 10, wherein the third portion comprises an inclined portion that is inclined with respect to the front surface of the mask body and that extends toward the first portion.

12. The mask apparatus according to claim 11, wherein the communication hole is disposed closer to the third portion than to the first portion.

13. The mask apparatus according to claim 1, further comprising a control substrate mounted on the mask body and configured to apply pressure to the cover portion,
wherein the pressure sensor is mounted on a rear surface of the control substrate.

14. The mask apparatus according to claim 13, wherein the cover portion defines a sensor opening that receives the pressure sensor.

15. The mask apparatus according to claim 13, further comprising a support rib that extends from the front surface of the mask body, the support rib comprising a hook disposed at an end of the support rib and configured to apply pressure to an upper end of the control substrate.

16. The mask apparatus according to claim 1, wherein the film is disposed between the pressure sensor and the communication hole.

17. The mask apparatus according to claim 1, wherein an outer surface of the extension portion is in contact with an inner surface of the sensor mounting portion.

18. The mask apparatus according to claim 1, further comprising a mask body cover that is coupled to the front surface of the mask body and covers the pressure sensor.

* * * * *